United States Patent
Jaroskova et al.

(10) Patent No.: US 8,563,591 B2
(45) Date of Patent: Oct. 22, 2013

(54) TRICYCLIC LACTAM DERIVATIVES AS 11-BETA HYDROXYSTEROID DEHYDROGENASE INHIBITORS

(75) Inventors: Libuse Jaroskova, Vosselaar (BE); Joannes Theodorus Maria Linders, Eindhoven (BE); Louis Jozef Elisabeth Van Der Veken, Vosselaar (BE); Gustaaf Henri Maria Willemsens, Beerse (BE)

(73) Assignee: Janssen Pharmaceutica N.V. (BE)

( * ) Notice: Subject to any disclaimer, the term of this patent is extended or adjusted under 35 U.S.C. 154(b) by 1403 days.

(21) Appl. No.: 11/661,468

(22) PCT Filed: Aug. 26, 2005

(86) PCT No.: PCT/EP2005/054198
§ 371 (c)(1),
(2), (4) Date: Feb. 26, 2007

(87) PCT Pub. No.: WO2006/024628
PCT Pub. Date: Mar. 9, 2006

(65) Prior Publication Data
US 2008/0214597 A1    Sep. 4, 2008

Related U.S. Application Data

(60) Provisional application No. 60/607,840, filed on Sep. 8, 2004.

(30) Foreign Application Priority Data

Aug. 30, 2004 (EP) .................................... 04104147

(51) Int. Cl.
C07D 209/62 (2006.01)
A61K 31/403 (2006.01)
A61K 31/404 (2006.01)

(52) U.S. Cl.
USPC ............. 514/411; 514/290; 546/79; 546/427

(58) Field of Classification Search
USPC ...................... 546/79; 514/290, 411; 548/427
See application file for complete search history.

(56) References Cited

U.S. PATENT DOCUMENTS

| | | | |
|---|---|---|---|
| 2,510,945 A | 6/1950 | Badgett et al. | |
| 2,524,643 A | 10/1950 | Walter et al. | |
| 3,526,656 A | 9/1970 | Butler | |
| 3,622,567 A | 11/1971 | Razdan | |
| 3,919,313 A | 11/1975 | Villani | |
| 5,356,907 A | 10/1994 | Clemence et al. | |
| 5,395,843 A | 3/1995 | Clemence et al. | |
| 5,541,343 A | 7/1996 | Himmelsbach et al. | |
| 5,559,130 A | 9/1996 | Clemence et al. | |
| 5,776,959 A | 7/1998 | Covey et al. | |
| 6,194,406 B1 | 2/2001 | Kane et al. | |
| 6,211,199 B1 | 4/2001 | Kane et al. | |
| 6,555,572 B2 | 4/2003 | Lauener et al. | |
| 7,332,524 B2 | 2/2008 | Linders et al. | |
| 7,687,644 B2 | 3/2010 | Jaroskova et al. | |
| 7,968,601 B2 | 6/2011 | Linders et al. | |
| 2001/0034343 A1 | 10/2001 | Maynard et al. | |
| 2003/0087952 A1 | 5/2003 | Wood et al. | |
| 2005/0245534 A1 | 11/2005 | Link et al. | |
| 2008/0064693 A1 | 3/2008 | Jaroskova et al. | |
| 2008/0139625 A1 | 6/2008 | Jaroskova et al. | |

FOREIGN PATENT DOCUMENTS

| | | |
|---|---|---|
| CA | 2017287 A1 | 11/1990 |
| DE | 1959898 A1 | 6/1970 |
| DE | 2624290 A | 4/1977 |
| EP | 117462 A2 | 9/1984 |
| EP | 0399814 A2 | 11/1990 |
| EP | 437120 B2 | 8/1995 |

(Continued)

OTHER PUBLICATIONS

Baussane et al., "Asymmetric synthesis of 3-substituted pyrrolidones via α-alkylation of a chiral non-racemic γ-lactam.", Tetrahedron: Asymmetry, 1998, pp. 797-804, vol. 9(5).

(Continued)

Primary Examiner — Rita Desai

(57) ABSTRACT the N-oxide forms, the pharmaceutically acceptable addition salts and the stereochemically isomeric forms thereof, wherein
X represents C or N;
Y represents C or N;
L represents a methyl or a direct bond;
$Z^1$ represents a direct bond, $C_{1-2}$alkyl- or a divalent radical of formula —$CH_2$—CH= (a) or —CH= (b);
$Z^2$ represents a direct bond, $C_{1-2}$alkyl- or a divalent radical of formula —$CH_2$—CH= (a) or —CH= (b);
$R^1$ represents hydrogen, halo, cyano, amino, phenyl, hydroxy, $C_{1-4}$alkyloxycarbonyl, hydroxycarbonyl, $NR^3R^4$ or $C_{1-4}$alkyl optionally substituted with one or more substituents selected from hydroxycarbonyl, phenyl, $C_{1-4}$alkyloxy or $NR^5R^6$ or $R^1$ represents $C_{1-4}$alkyloxy- optionally substituted with one or more substituents selected from hydroxycarbonyl, phenyl, $C_{1-4}$alkyloxy or $NR^7R^8$;
$R^2$ represents hydrogen, halo, $C_{1-4}$alkyl or $C_{1-4}$alkyloxy-;
$R^3$ and $R^4$ each independently represent hydrogen, $C_{1-4}$alkyl or $C_{1-4}$alkylcarbonyl-;
$R^5$ and $R^6$ each independently represent hydrogen, $C_{1-4}$alkyl or $C_{1-4}$alkylcarbonyl-;
$R^7$ and $R^8$ each independently represent hydrogen, $C_{1-4}$alkyl or $C_{1-4}$alkylcarbonyl-;
A represents phenyl or a monocyclic heterocycle selected from the group consisting of thiophenyl, furanyl, oxazolyl, thiazolyl, imidazolyl, isoxazolyl, isothiazolyl, pyrridinyl, pyridazinyl, pyrimidinyl and piperazinyl.

(I)

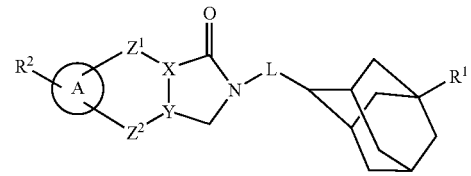

14 Claims, No Drawings

(56) References Cited

FOREIGN PATENT DOCUMENTS

| | | |
|---|---|---|
| EP | 00481522 B1 | 12/1997 |
| EP | 1127883 A | 8/2001 |
| EP | 0873336 B1 | 3/2003 |
| FR | 1399615 | 4/1965 |
| FR | 2714291 A | 6/1995 |
| GB | 1065533 | 4/1967 |
| GB | 2136801 A | 12/1984 |
| JP | 59 164779 | 9/1984 |
| JP | 59 175472 A | 10/1984 |
| JP | 03 086853 | 4/1991 |
| JP | 9 501650 | 2/1997 |
| JP | 11 506471 | 6/1999 |
| WO | 95/00493 A1 | 1/1995 |
| WO | WO 97/19074 A1 | 5/1997 |
| WO | WO 97/22604 A1 | 6/1997 |
| WO | 98/11073 A1 | 3/1998 |
| WO | 96/04254 A | 6/1999 |
| WO | 99/26927 A2 | 6/1999 |
| WO | 01/23399 A1 | 4/2001 |
| WO | 01/90090 A1 | 11/2001 |
| WO | WO 03/065983 | 8/2003 |
| WO | 03/104207 A2 | 12/2003 |
| WO | 2004/056745 A2 | 7/2004 |
| WO | WO 2004/056744 | 7/2004 |
| WO | WO 2004/065351 | 8/2004 |
| WO | 2004/089470 | 10/2004 |
| WO | WO 2004/089415 A2 | 10/2004 |
| WO | WO 2004/089416 A2 | 10/2004 |
| WO | 2004/075847 A2 | 9/2007 |

OTHER PUBLICATIONS

Blommaert et al., "Mono and Sequential BIS Solid Phase Alkylations of a (R)-Phenylglycinol Derived Pyrrolidinone Scaffold.", Heterocycles, 2001, pp. 2273-2278, vol. 55(12).

Larsen et al., "A Modified Bischler-Napieralski Procedure for the Synthesis of 3-Aryl-3,4-dihydroisoquinolines.", Journal of Organic Chemistry, 1991, pp. 6034-6038, vol. 56(21), American Chemical Society.

Masuzaki et al., "A Transgenic Model of Visceral Obesity and the Metabolic Syndrome.", Science, 2001, pp. 2166-2170, vol. 294.

Montague et al., "Perspective in Diabetes. The Perils of Portliness. Causes and Consequences of Visceral Adiposity.", Diabetes, 2000, pp. 883-888, vol. 49.

Rauz et al., "Expression and Putative Role of 11β-Hydroxysteroid Dehydrogenase Isozymes within the Human Eye.", Invest. Ophtalmol. Vis. Science, Aug. 2001, pp. 2037-2042, vol. 42(9).

Stewart et al., "Cortisol, 11β-hydroxysteroid dehydrogenase type 1 and central obesity.", Trends. Endrocrin. Metabol., 2002, pp. 94-96, vol. 13.

Zhou et al., "Glucocorticoid effects on extracellular matrix proteins and integrins in bovine trabecular meshwork cells in relation to glaucoma.", Int. J. Mol. Med., 1998, pp. 339-346, vol. 1.

Rufer C. et al: "Neue Acylierte 2-(4-Aminiophenyl)-Propionsaeuren ALS Potentiele Antiplogistica" European Journal of Medicinal Chemistry, Editions Scientifique Elsevier,Paris, FR, vol. 13, No. 2, Mar. 1978, pp. 193-198.

Chemical Abstract: Database Beilstein, Database accession No. 5949999, Schmitz, E. et al (1982).

Murahashi, S.: "Synthesis of Phthalimidines from Schiff Bases and Carbon Monoxide" J. Am. Chem. Soc., vol. 77, 1955, pp. 6403-6404.

Katritzky, A. et al "Novel syntheses of enantiopure hexahydroimidazo[1,5-b]isoquinolines and tetrahydroimidazo[1,5-b]isoquinolin-1(5H)-ones via iminium cation cyclizations" J. Org. Chem., vol. 67, 2002, pp. 8224-8229.

Chemical Abstract: Database Beilstein, Database accession No. 1481016, and 1481024, Amano, 1966.

Chemical Abstract: Database CAPLUS, Database accession No. 1966:71362 Amano, T. 1966.

PCT International Search Report dated Dec. 23, 2005 for PCT Application. No. PCT/EP2005/054198 which relates to U.S. Patent Application filed herewith.

Written Opinion of the International Searching Authority for PCT Application No. PCT/EP2005/054198.

Boyle, Craig D., "Recent advances in the discovery of 11β-HSD1 inhibitors.", Current Opinion in Drug Discovery & Development, 2008, 11(4), pp. 495-511, The Thompson Corporation.

Chapman et al., "11β-HSD1, inflammation, metabolic disease and age-related cognitive (dys)function.", Neurochemical Research, 2008, pp. 624-636, vol. 33, Springer Science+Business Media.

Hughes et al., "11-Beta-hydroxysteroid dehydrogenase type 1 (11β-HSD1) inhibitors in Type 2 diabetes mellitus and obesity.", Expert Opinion. Investig. Drugs, 2008, pp. 481-496, vol. 17, (4), Informa Healthcare, UK.

Wamil et al., "Inhibition of 11β-hydroxysteroid dehydrogenase type 1 as a promising therapeutic target.", Drug Discovery Today, Jul. 2007, pp. 504-520, vol. 12, (13/14), Elsevier.

Yau et al., "Targeting 11β-hydroxysteroid dehydrogenase type 1 in brain: therapy for cognitive aging?", Expert Review of Endocrinology & Metabolism, 2006, pp. 527-536, vol. 1 (4), Future Drugs Ltd.

"Incyte's Selective Oral Inhibitor of 11beta-HSD1 demonstrates improvements in insulin sensitivity and lowers cholesterol levels in type 2 diabetics." About Incyte: Press Release, Incyte Corporation website, http://investor.incyte.com, Jun. 9, 2008.

Aicher et al., "Kappa Opioid Receptor (KOR) and GAD67 Immunoreactivity Are Found in Off and Neutral Cells in the Rostral Ventromedial Medulla.", J. Neurophysiol, 2006, pp. 3465-3473, vol. 96.

Amgen-Investors-Pipeline; http://www.amgen.com/investors/pipe_AMG221.html (1 page), 2008.

Apria-Resources-news; http://www.apria.com/resources/1,2725,494-769212,00.html (4 pages), 2008.

Arzel et al., Assymetrie Tetrahedron1999, pp. 3877-3881, vol. 10(20), XP001203518.

Avdyunina et al., "N-Adamantylamides of benzimidazoline-3-acetic acids: synthesis and pharmacological properties" Khimiko-Farmatsevticheskii Zhurnal, 1988, pp. 819-822, vol. 22(7), XP008042581.

Badman et al., "The Gut and Energy Balance, Visceral Allies in the Obesity Wars.", Science, Mar. 25, 2005, pp. 1909-1014, vol. 307.

Bonnekessel et al., "Beilstein Institut zur Foerderung der Chemischen Wissenschaften Frankfurt am Main, DE". Chem. Ber. 1973, pp. 2890-2903, vol. 106, XP002248049.

Caglioti et al., Beilstein Institut zur Foerderung der Chemischen Wissenschaften Frankfurt am Main, DE' J. Ora. Chem., 1968, pp. 2979-2781, vol. 33(7), XP002248043.

Camps, Beilstein Institut zur Foerderung der Chemischen Wissenschaften, Frankfurt am Main, DE. Arch. Pharm.; 1902, p. 358, vol. 240, XP002248047.

Chemical Abstract: Database Chemcats (Apr. 23, 2003) Database accession No. 2001:711911; XP002316807.

Chemical Abstract: Database Chemcats (Apr. 25, 2003) Database accession No. 2001:2280339; XP002316809.

Chemical Abstract: Database Chemcats (Aug. 11, 2003) Database accession No. 2001:1353682; XP002316808.

Chemical Abstract: Database Chemcats (Oct. 20, 2003) Database accession No. 2002:1350205 XP002316810.

Chemical Abstract: Database Chemcats (Oct. 20, 2013) Database accession No. 2002:1350218; XP002316811.

Chemical Abstract: Database Chemcats an 2002: 1350644; Oct. 2003; XP002354668, Abstract.

Division of Medical Chemistry Abstracts-234th ACS National Meeting Boston, MA, Aug. 19-23, 2007.

Forster, A., "Beilstein Institut zur Foerderung der Chemischen Wissenschaften Frankfurt am Main, DE". J. Chem. Soc. 1904, p. 1190, vol. 85, XP-002248034.

Garcia-Valverde et al., "A Diastereoselective Approach to Enantiopure 3-Substituted Pyrrolidines from Masked Lithium Homoenolates from Norephedrine.", Tetrahedron, 1996, pp. 10761-10770, vol. 52(32).

(56) References Cited

OTHER PUBLICATIONS

Giuliano, L., "Beilstein Institut zur Foerderung der Chemischen Wissenschaften Frankfurt am Main, DE", *Farmaco*, 1952, pp. 29-32, vol. 7, XP002248051.

Gryszkiewicz-T., "Beilstein Institut zur Foerderung der Chemischen Wissenschaften Frankfurt am Main, DE", *Rocz. Chem*, 1934, pp. 335-337, vol. 14, XP002248048.

Jones et al., "Beilstein Institut zur Foerderung der Chemischen Wissenschaften Frankfurt am Main, DE". *Tetrahedron*, 1965, pp. 2961-2966, vol. 21, XP002279296.

Kitagawa, O. et al., "Beilstein Institut zur Foerderung der Chemischen Wissenschaften Frankfurt am Main, DE". *Tetrahedron Lett.*, 1999, pp. 8827-8832, vol. 40(50), XP002279294.

Knunjanz, G. "Beilstein Institut zur Foerderung der Chemischen Wissenschaften Frankfurt am Main, DE", *IASKA6*, 1958, pp. 1219-1221, XP002248040.

Koenig et al., "Beilstein Institut zur Foerderung der Chemischen Wissenschaften Frankfurt am Main, DE". Chem. Ber., 1965, pp. 3172-3723, vol. 98, XP002248046.

Koetz, M., "Beilstein Institut zur Foerderung der Chemischen Wissenschaften Frankfurt am Main, DE". *J. Prakt. Chem*. 1926, p. 74, vol. 113, XP-002248036.

Kuehne, M. E., et al., "Beilstein Institut zur Foerderung der Chemischen Wissenschaften Frankfurt am Main, DE". *J. Org. Chem.*, 1977, pp. 2082-2087, vol. 42(12), XP002248045.

Latypov, S. et al., "Determination of the absolute stereochemistry of alcohols and amines by NMR of the group directly linked to the chiral derivatizing reagent". *Tetrahedron*, 2001, pp. 2231-2236, vol. 57(11), XP004230761.

Lavrova et al., *Zhurnal Organicheskoi Khimii*, 1974, pp. 761-765, vol. 10(4).

Markownikow "Beilstein Institut zur Foerderung der Chemischen Wissenschaften, Frankfurt am Main, DE". *Chem. Ber.*, 1892, pp. 3357, vol. 25, XP-002248035.

Mizuno, K., "Beilstein Institut zur Foerderung der Chemischen Wissenschaften Frankfurt am Main, DE". *J. Chem. Soc. Chem. Commun*. 1975, p. 308.XP002248042.

Nikiforov et al., "Synthesis and Absolute Configuration of Diastereomeric 3-Substituted 1-[1'(S)-Phenylethy1]-2-Pyrrolidinones.", *Doklady Bolgarskoi Akademii Nauk*, 1986, pp. 73-76, vol. 39(3).

Oda et al., "An efficient route to chiral, non-racemic 3-alkyl-3-arylpyrrolidines. Improved stereoselectivity in alkylation of bicyclic lactams and the effect of leaving groups.", *Tetrahedron Letters*, 2000, pp. 8193-8197, vol. 41(43).

Olah et al., "Beilstein Institut zur Foerderung der Chemischen Wissenschaften Frankfurt am Main, DE". *Synthesis*, 1979, pp. 274-76, XP002248039.

Olsen, C. E., "Beilstein Institut zur Foerderung der Chemischen Wissenschaften Frankfurt am Main, DE". *Acta Chem*. Scand. Ser. B., 1975, pp. 953-62, XP002248044.

Pharmas-Cutting-Edge; http://pharmaweblog.com/blog/category/rd/preclinical (1 page), 2007.

Pop et al., "Versatile Acylation of N-Nucleophiles Using a New Polymer-Supported 1-Hydroxybenzotriazole Derivative.", *J. Orq. Chem.*, 1997, pp. 2594-2603, vol. 62.

Sabri et al., "Synthesis and antibacterial activity of some new N-(3-methyl-2-quinoxaloyl) amino alcohols and amine 1,4-dioxides". *J. Chem. Eng.* Data, 1984, pp. 229-31, vol. 29(2), XP002279298.

Schroth et al., "Beilstein Institut zur Foerderung der Chemischen Wissenschaften Frankfurt am Main, DE". *J. Prakt. Chem.*, 1983, pp. 787-802, vol. 325(5), XP002248035.

Starnes et al., "Beilstein Institut zur Foerderung der Chemischen Wissenschaften Frankfurt am Main, DE". *J. Amer. Chem. Soc*., 2001, pp, 4659-4669, vol. 123(20), XP002248037.

Sugasawa et al., "Beilstein Institut zur Foerderung der Chemischen Wissenschaften Frankfurt am Main, DE". 1952, p. 7461, vol. 72, XP002248038.

Takahashi, T., "Synthesis of analgesics. XX. Camphane derivatives.", *Chem. Abst.*, 1959, p. 165-166, vol. 79, XP002248033.

Terauchi et al., "Beilstein Institut zur Foerderung der Chemischen Wissenschaften Frankfurt am Main, DE". *Tetrahedron*, 2003, pp. 587-592, vol. 14(5), XP002279295.

Treatment of Dementia: Anything New ?; http://www.medscape.com/viewarticle/547499_print (8 pages), 2006.

Yamato et al., "Beilstein Institut zur Foerderung der Chemischen Wissenschaften Frankfurt am Main, DE". *Chem. Pharm. Bull.*, 1988, pp. 3453-3461, vol. 36(9), XP002279297.

Young, C., "Beilstein Institut zur Foerderung der Chemischen Wissenschaften, Frankfurt am Main, DE". *J. Chem. Soc.*, 1898, p. 365, vol. 73, XP-002248041.

TRICYCLIC LACTAM DERIVATIVES AS 11-BETA HYDROXYSTEROID DEHYDROGENASE INHIBITORS

CROSS REFERENCE TO RELATED APPLICATIONS

This application is the US national stage of Application No. PCT/EP2005/054198, filed Aug. 26, 2005, which application claims priority from EP 04104147.6, filed Aug. 30, 2004 and U.S. Application No. 60/607,840, filed Sep. 8, 2004.

The metabolic syndrome is a disease with increasing prevalence not only in the Western world but also in Asia and developing countries. It is characterised by obesity in particular central or visceral obesity, type 2 diabetes, hyperlipidemia, hypertension, arteriosclerosis, coronary heart diseases and eventually chronic renal failure (C. T. Montague et al. (2000), Diabetes, 49, 883-888).

Glucocorticoids and 11β-HSD1 are known to be important factors in differentiation of adipose stromal cells into mature adipocytes. In the visceral stromal cells of obese patients, 11β-HSD1 mRNA level is increased compared with subcutaneous tissue. Further, adipose tissue over-expression of 11β-HSD1 in transgenic mice is associated with increased corticosterone levels in the adipose tissue, visceral obesity, insulin sensitivity, Type 2 diabetes, hyperlipidemia and hyperphagia (H. Masuzaki et al (2001), Science, 294, 2166-2170). Therefore, 11β-HSD1 is most likely be involved in the development of visceral obesity and the metabolic syndrome.

Inhibition of 11β-HSD1 results in a decrease in differentiation and an increase in proliferation of adipose stromal cells. Moreover, glucocorticoid deficiency (adrenalectomy) enhances the ability of insulin and leptin to promote anorexia and weight loss, and this effect is reversed by glucocorticoid administration (P. M. Stewart et al (2002), Trends Endocrin. Metabol, 13, 94-96). These data suggest that enhanced reactivation of cortisone by 11β-HSD1 may exacerbate obesity and it may be beneficial to inhibit this enzyme in adipose tissue of obese patients.

Obesity is also linked to cardiovascular risks. There is a significant relationship between cortisol excretion rate and HDL cholesterol in both men and women, suggesting that glucocorticoids regulate key components of cardiovascular risk. In analogy, aortic stiffness is also associated with visceral adiposity in older adults.

The impact of the effect of decreased 11β-HSD1 activity is highlighted by the β-HSD1 knockout mouse that has increased plasma levels of endogenous active glucocorticoid, but inspite of this remains protected from insulin resistance induced by stress and obesity. Additionally, these knockout mouse present an anti-atherogenic plasmid lipid profile and benefits from decreased age-related cognitive impairment.

Glucocorticoids and Glaucoma

Glucocorticoids increase the risk of glaucoma by raising the intraocular pressure when administered exogenously and in certain conditions of increased production like in Cushing's syndrome. Corticosteroid-induced elevation of intra ocular pressure is caused by increased resistance to aqueous outflow due to glucocorticoid induced changes in the trabecular meshwork and its intracellular matrix. Zhou et al. (Int J Mol Med (1998) 1, 339-346) also reported that corticosteroids increase the amounts of fibronectin as well as collagen type I and type IV in the trabecular meshwork of organcultured bovine anterior segments.

11β-HSD1 is expressed in the basal cells of the corneal epithelium and the non-pigmented epithelial cells. Glucocorticoid receptor mRNA was only detected in the trabecular meshwork, whereas in the non-pigmented epithelial cells mRNA for the glucocorticoid-, mineralocorticoid receptor and 11β-HSD1 was present. Carbenoxolone administration to patients resulted in a significant decrease in intra-ocular pressure (S. Rauz et al. (2001), Invest. Ophtalmol. Vis. Science, 42, 2037-2042), suggesting a role for HSD1-inhibitors in treating glaucoma.

Accordingly, the underlying problem to be solved by the present invention was to identify potent 11β-HSD inhibitors, with a high selectivity for 11β-HSD1, and the use thereof in treating pathologies associated with excess cortisol formation, i.e. disorders where a decreased level of active glucocorticoid is desirable, such as metabolic syndrome, type 2 diabetes, impaired glucose tolerance (IGT), impaired fasting glucose (IFG), dyslipidemia, hypertension, obesity, diabetes, obesity related cardiovascular diseases, arteriosclerosis, atherosclerosis, myopathy, osteoporosis, neurodegenerative and psychiatric disorders, stress related disorders and glaucoma. As shown hereinbelow, the 3-substituted 2-pyrrolidinone derivatives of formula (I) were found to be useful as a medicine, in particular in the manufacture of a medicament for the treatment of pathologies associated with excess cortisol formation.

Blommaert A. et al. (Heterocycles (2001), 55(12), 2273-2278) provides the preparation of piperidine- and pyrrolidinone-like polymer supported (R)-phenylglycinol-derived scaffolds and in particular discloses 2-Pyrrolidinone, 1-[(1R)-2-hydroxy-1-phenylethyl]-3-methyl-3-(phenylmethyl)- and 2-Pyrrolidinone, 1-[(1R)-2-hydroxy-1-phenylethyl]-3-(phenylmethyl)-, (3R).

Bausanne I. et al. (Tetrahedron: Asymmetry (1998), 9(5), 797-804) provides the preparation of 3-substituted pyrrolidinones via α-alkylation of a chiral non-racemic γ-lacton and in particular discloses 1-(2-hydroxy-1-phenylethyl)-3-benzylpyrrolidin-2-one.

US 2001/034343; U.S. Pat. No. 6,211,199; U.S. Pat. No. 6,194,406; WO 97/22604 and WO 97/19074 are a number of patent applications filed by Aventis Pharmaceuticals Inc. providing 4-(1H-benzimidazol-2-yl)[1,4]diazepanes useful for the treatment of allergic diseases. In these applications the 3-substituted pyrrolidinones of the present invention are disclosed as intermediates in the synthesis of said 4-(1H-benzimidazol-2-yl)[1,4]-diazepanes. These applications in particular disclose; 2-Pyrrolidinone, 3-[(4-fluorophenyl)methyl]-1-[(1S)-1-phenylethyl]- and 2-Pyrrolidinone, 3-[(4-fluorophenyl)-methyl]-1-[(1R)-1-phenylethyl]-.

Adamantyl like compounds are also disclosed in PCT publication WO 03065983 (Merck & Co., Inc.) and WO 2004056744 (Janssen Pharmaceutica N.V.). Taking WO 2004056744 as the closest prior art, the compounds of the present application differ in that the adamantyl ring is linked to a ring amide nitrogen being part of a tricyclic system. Notwithstanding the fact that WO 03065983 discloses that the adamantyl ring may be directly linked to a tricyclic ring system, it should be noted that said tricyclic ring systems are characterised in having 2-adamantyl-triazole as a core structural element and that it was accordingly not to be expected that replacing the triazole with a imidazolidinone or pyrrolidinone could be done without loss of the desired activity, i.e. potent 11β-HSD inhibitors, with a selectivity for 11β-HSD1.

Hence, in none of the cited documents the therapeutic application of the tricyclic adamantylamide derivatives of the present invention has been disclosed nor suggested. Accordingly, in a first aspect this invention concerns compounds of formula (I)

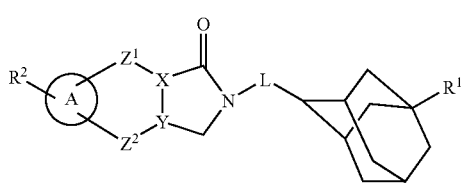

(I)

the N-oxide forms, the pharmaceutically acceptable addition salts and the stereochemically isomeric forms thereof, wherein X represents C or N;
Y represents C or N;
L represents a methyl or a direct bond;
$Z^1$ represents a direct bond, $C_{1-2}$alkyl- or a divalent radical of formula —$CH_2$—CH= (a) or —CH= (b);
$Z^2$ represents a direct bond, $C_{1-2}$alkyl- or a divalent radical of formula —$CH_2$—CH= (a) or —CH= (b);
$R^1$ represents hydrogen, halo, cyano, amino, phenyl, hydroxy, $C_{1-4}$alkyloxycarbonyl, —O—(C=O)—$C_{1-4}$alkyl, hydroxycarbonyl, $NR^3R^4$ or $C_{1-4}$alkyl wherein said $C_{1-4}$alkyl or —O—(C=O)—$C_{1-4}$alkyl are optionally substituted with one or more substituents selected from halo, hydroxycarbonyl, phenyl, $C_{1-4}$alkyloxy or $NR^5R^6$ or $R^1$ represents $C_{1-4}$alkyloxy- optionally substituted with one or more substituents selected from halo, hydroxycarbonyl, phenyl, $C_{1-4}$alkyloxy or $NR^7R^8$;
$R^2$ represents hydrogen, halo, $C_{1-4}$alkyl or $C_{1-4}$alkyloxy-;
$R^3$ and $R^4$ each independently represent hydrogen, $C_{1-4}$alkyl or $C_{1-4}$alkylcarbonyl-;
$R^5$ and $R^6$ each independently represent hydrogen, $C_{1-4}$alkyl or $C_{1-4}$alkylcarbonyl-;
$R^7$ and $R^8$ each independently represent hydrogen, $C_{1-4}$alkyl or $C_{1-4}$alkylcarbonyl-;
A represents phenyl or a monocyclic heterocycle selected from the group consisting of thiophenyl, furanyl, oxazolyl, thiazolyl, imidazolyl, isoxazolyl, isothiazolyl, pyrridinyl, pyridazinyl, pyrimidinyl and piperazinyl.

As used hereinafter the compounds of formula (I) refers to the compounds according to the present invention including the compounds of formula ($I^{bis}$), ($I^i$), ($I^{ii}$), ($I^{iii}$), ($I^{iv}$) and their pharmaceutically acceptable N-oxides, addition salts, quaternary amines and the stereochemically isomeric forms.

As used in the foregoing definitions and hereinafter, halo is generic to fluoro, chloro, bromo and iodo; $C_{1-2}$alkyl defines straight saturated hydrocarbon radicals having from 1 to 2 carbon atoms, i.e. methyl or ethyl; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like; $C_{1-4}$alkyloxy defines straight or branched saturated hydrocarbon radicals having form 1 to 4 carbon atoms such as methoxy, ethoxy, propyloxy, butyloxy, 1-methylethyloxy, 2-methylpropyloxy and the like.

The heterocycles as mentioned in the above definitions and hereinafter may be attached to the remainder of the molecule of formula (I) through any ring carbon or heteroatom as appropriate. Thus, for example, when the heterocycle is imidazolyl, it may be a 1-imidazolyl, 2-imidazolyl, 3-imidazolyl, 4-imidazolyl and 5-imidazolyl; when it is thiazolyl, it may be 2-thiazolyl, 4-thiazolyl and 5-thiazolyl.

The pharmaceutically acceptable addition salts as mentioned hereinabove are meant to comprise the therapeutically active non-toxic acid addition salt forms, which the compounds of formula (I), are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are meant to comprise the therapeutically active non-toxic base addition salt forms which the compounds of formula (I), are able to form. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine.

Conversely said salt forms can be converted by treatment with an appropriate base or acid into the free acid or base form.

The term addition salt as used hereinabove also comprises the solvates which the compounds of formula (I), as well as the salts thereof, are able to form. Such solvates are for example hydrates, alcoholates and the like.

The term stereochemically isomeric forms as used hereinbefore defines the possible different isomeric as well as conformational forms which the compounds of formula (I), may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I), both in pure form or in admixture with each other are intended to be embraced within the scope of the present invention.

The N-oxide forms of the compounds of formula (I) are meant to comprise those compounds of formula (I) wherein one or several nitrogen atoms are oxidized to the so-called N-oxide.

A first group of compounds are those compounds of formula (I) wherein one or more of the following restrictions apply;
(i) X represents C or N;
(ii) Y represents C or N;
(iii) L represents a methyl or a direct bond;
(iv) $Z^1$ represents a direct bond, $C_{1-2}$alkyl- or a divalent radical of formula —$CH_2$—CH= (a) or —CH= (b);
(v) $Z^2$ represents a direct bond, $C_{1-2}$alkyl- or a divalent radical of formula —$CH_2$—CH= (a) or —CH= (b);
(vi) $R^1$ represents hydrogen, halo, cyano, amino, phenyl, hydroxy, $C_{1-4}$alkyloxycarbonyl, hydroxycarbonyl, $NR^3R^4$ or $C_{1-4}$alkyl optionally substituted with one or more substituents selected from hydroxycarbonyl, phenyl, $C_{1-4}$alkyloxy or $NR^5R^6$ or $R^1$ represents $C_{1-4}$alkyloxy- optionally substituted with one or more substituents selected from hydroxycarbonyl, phenyl, $C_{1-4}$alkyloxy or $NR^7R^8$;
(vii) $R^2$ represents hydrogen, halo, $C_{1-4}$alkyl or $C_{1-4}$alkyloxy-;
(viii) $R^3$ and $R^4$ each independently represent hydrogen, $C_{1-4}$alkyl or $C_{1-4}$alkylcarbonyl-;
(ix) $R^5$ and $R^6$ each independently represent hydrogen, $C_{1-4}$alkyl or $C_{1-4}$alkylcarbonyl-;

(x) R⁷ and R⁸ each independently represent hydrogen, $C_{1-4}$alkyl or $C_{1-4}$alkylcarbonyl-;
(xi) A represents phenyl or a monocyclic heterocycle selected from the group consisting of thiophenyl, furanyl, oxazolyl, thiazolyl, imidazolyl, isoxazolyl, isothiazolyl, pyrridinyl, pyridazinyl, pyrimidinyl and piperazinyl.

An interesting group of compounds are those compounds of formula (I) wherein one or more of the following restrictions apply;
(i) X represents C or N;
(ii) Y represents C or N;
(iii) L represents a methyl or a direct bond;
(iv) $Z^1$ represents a direct bond, $C_{1-2}$alkyl- or a divalent radical of formula —CH₂—CH= (a) or —CH= (b);
(v) $Z^2$ represents a direct bond, $C_{1-2}$alkyl- or a divalent radical of formula —CH₂—CH= (a) or —CH= (b);
(vi) R¹ represent hydrogen, halo, cyano, amino, phenyl, hydroxy, $C_{1-4}$alkyloxycarbonyl-, hydroxycarbonyl, NR³R⁴ or $C_{1-4}$alkyl substituted with one or more substituents selected from hydroxycarbonyl, phenyl, $C_{1-4}$alkyloxy or NR⁵R⁶;
(vii) R² represents hydrogen, halo, $C_{1-4}$alkyl or $C_{1-4}$alkyloxy-;
(viii) R³ and R⁴ each independently represent hydrogen, $C_{1-4}$alkyl or $C_{1-4}$alkylcarbonyl-;
(ix) R⁵ and R⁶ each independently represent hydrogen, $C_{1-4}$alkyl or $C_{1-4}$alkylcarbonyl-.
(x) A represents phenyl or a monocyclic heterocycle selected from the group consisting of thiophenyl, furanyl, oxazolyl, thiazolyl, imidazolyl, isoxazolyl, isothiazolyl, pyrridinyl, pyridazinyl, pyrimidinyl and piperazinyl A further interesting group of compounds consists of those compounds of formula (I) wherein one or more of the following restrictions apply:
(i) L represents methyl or a direct bond;
(ii) R¹ represents hydrogen, halo or hydroxy; in particular halo or hydroxyl;
(iii) R² represents hydrogen, halo or $C_{1-4}$alkyloxy-;
(iv) A represents phenyl or a monocyclic heterocycle selected from the group consisting of pyridinyl and thiophenyl;

Another group of compounds consists of those compounds of formula (I) wherein one or more of the following restrictions apply:
(i) L represents methyl or a direct bond;
(ii) R¹ represents hydrogen, halo, amino or hydroxy; in particular fluoro, amino or hydroxyl;
(iii) R² represents hydrogen, bromo or methoxy-;
(iv) $Z^1$ represents a direct bond, methyl, ethyl or a divalent radical of formula —CH₂—CH= (a);
(v) $Z^2$ represents a direct bond, methyl or ethyl;
(vi) A represents phenyl or a monocyclic heterocycle selected from the group consisting of pyridinyl and thiophenyl;

Also of interest are those compounds of formula (I) wherein
A represents phenyl or pyridinyl and wherein L represents a direct bond; and/or
R¹ represents halo, cyano, amino, phenyl, hydroxy, $C_{1-4}$alkyloxycarbonyl-, hydroxycarbonyl, NR³R⁴ or $C_{1-4}$alkyl optionally substituted with one or more substituents selected from hydroxycarbonyl, phenyl, $C_{1-4}$alkyloxy or NR⁵R⁶ or R¹ represents $C_{1-4}$alkyloxy- optionally substituted with one or more substituents selected from hydroxycarbonyl, phenyl, $C_{1-4}$alkyloxy or NR⁷R⁸; in particular R¹ represents halo, cyano, amino, phenyl, hydroxy, $C_{1-4}$alkyloxycarbonyl-, hydroxycarbonyl, NR³R⁴ or $C_{1-4}$alkyl substituted with one or more substituents selected from hydroxycarbonyl, phenyl, $C_{1-4}$alkyloxy or NR⁵R⁶.

In a preferred embodiment the compounds of formula (I) are selected from the group consisting of;
2-Adamantan-2-yl-2,3,3a,4,9,9a-hexahydro-benzo[f]isoindol-1-one;
2-Adamantan-2-yl-2,3,10,10a-tetrahydro-5H-imidazo[1,5-b]isoquinolin-1-one;
2-Adamantan-2-yl-1,5,10,10a-tetrahydro-2H-imidazo[1,5-b]isoquinolin-3-one;
2-Adamantan-1-ylmethyl-1,2,3a,4,5,9b-hexahydro-benzo[e]isoindol-3-one;
7-Adamantan-2-yl-7,8,8a,9-tetrahydro-pyrrolo[3,4-g]quinolin-6-one;
2-(5-Hydroxy-adamantan-2-yl)-1,5,6,10b-tetrahydro-2H-imidazo[5,1-a]isoquinolin-3-one;
2-(5-Fluoro-adamantan-2-yl)-1,2,3a,4,5,9b-hexahydro-benzo[e]isoindol-3-one;
2-(5-Hydroxy-adamantan-2-yl)-2,3,3a,4,9,9a-hexahydro-benzo[f]isoindol-1-one.

In a further embodiment the present invention provides compounds of formula ($I^{bis}$)

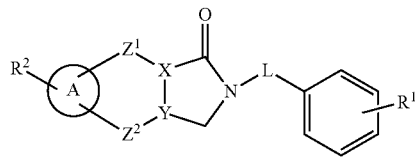

the N-oxide forms, the pharmaceutically acceptable addition salts and the stereochemically isomeric forms thereof, wherein
X represents C or N;
Y represents C or N;
L represents a methyl or a direct bond;
$Z^1$ represents a direct bond, $C_{1-2}$alkyl- or a divalent radical of formula —CH₂—CH= (a) or —CH= (b);
$Z^2$ represents a direct bond, $C_{1-2}$alkyl- or a divalent radical of formula —CH₂—CH= (a) or —CH= (b);
R¹ represents hydrogen, halo, cyano, amino, phenyl, hydroxy, $C_{1-4}$alkyloxycarbonyl, —O—(C=O)—$C_{1-4}$alkyl, hydroxycarbonyl, NR³R⁴ or $C_{1-4}$alkyl wherein said $C_{1-4}$alkyl or —O—(C=O)—$C_{1-4}$alkyl are optionally substituted with one or more substituents selected from halo, hydroxycarbonyl, phenyl, $C_{1-4}$alkyloxy or NR⁵R⁶ or
R¹ represents $C_{1-4}$alkyloxy- optionally substituted with one or more substituents selected from halo, hydroxycarbonyl, phenyl, $C_{1-4}$alkyloxy or NR⁷R⁸;
R² represents hydrogen, halo, $C_{1-4}$alkyl or $C_{1-4}$alkyloxy-;
R³ and R⁴ each independently represent hydrogen, $C_{1-4}$alkyl or $C_{1-4}$alkylcarbonyl-;
R⁵ and R⁶ each independently represent hydrogen, $C_{1-4}$alkyl or $C_{1-4}$alkylcarbonyl-;
R⁷ and R⁸ each independently represent hydrogen, $C_{1-4}$alkyl or $C_{1-4}$alkylcarbonyl-;
A represents phenyl or a monocyclic heterocycle selected from the group consisting of thiophenyl, furanyl, oxazolyl, thiazolyl, imidazolyl, isoxazolyl, isothiazolyl, pyrridinyl, pyridazinyl, pyrimidinyl and piperazinyl.

In particular the compounds of formula ($I^{bis}$) wherein one or more of the following restrictions apply;
(i) X represents C or N;
(ii) Y represents C or N;
(iii) L represents a methyl or a direct bond;
(iv) $Z^1$ represents a direct bond, $C_{1-2}$alkyl- or a divalent radical of formula —$CH_2$—CH= (a) or —CH= (b);
(v) $Z^2$ represents a direct bond, $C_{1-2}$alkyl- or a divalent radical of formula —$CH_2$—CH= (a) or —CH= (b);
(vi) $R^1$ represent hydrogen, halo, cyano, amino, phenyl, hydroxy, $C_{1-4}$alkyloxycarbonyl-, hydroxycarbonyl, $NR^3R^4$ or $C_{1-4}$alkyl substituted with one or more substituents selected from hydroxycarbonyl, phenyl, $C_{1-4}$alkyloxy or $NR^5R^6$; in particular $R^1$ represents hydrogen, halo, amino or hydroxy; even more particular fluoro, amino or hydroxyl;
(vii) $R^2$ represents hydrogen, halo, $C_{1-4}$alkyl or $C_{1-4}$alkyloxy-; in particular $R^2$ represents hydrogen, halo or $C_{1-4}$alkyloxy-;
(viii) $R^3$ and $R^4$ each independently represent hydrogen, $C_{1-4}$alkyl or $C_{1-4}$alkylcarbonyl-;
(ix) $R^5$ and $R^6$ each independently represent hydrogen, $C_{1-4}$alkyl or $C_{1-4}$alkylcarbonyl-.
(x) A represents phenyl or a monocyclic heterocycle selected from the group consisting of thiophenyl, furanyl, oxazolyl, thiazolyl, imidazolyl, isoxazolyl, isothiazolyl, pyrridinyl, pyridazinyl, pyrimidinyl and piperazinyl; in particular A represents phenyl or a monocyclic heterocycle selected from the group consisting of pyridinyl and thiophenyl.

In a further aspect the present invention provides any of the aforementioned group of compounds for use as a medicine. In particular in the treatment or prevention of pathologies associated with excess cortisol formation such as obesity, diabetes, obesity related cardiovascular diseases, stress and glaucoma.

PCT International patent application WO 2004/089416 provides the benefits of a combination therapy comprising the administration of a 11β-HSD1 inhibitor and an antihypertensive agent in the treatment of e.g. insulin resistance, dyslipidemia, obesity and hypertension, in particular in the treatment of hypertension. It is accordingly an object of the present invention to provide any of the aforementioned group of compounds in a combination therapy with an antihypertensive agent, such as for example alprenolol, atenolol, timolol, pindolol, propranolol, metoprolol, bisoprololfumerate, esmolol, acebutelol, acebutolol, betaxolol, celiprolol, nebivolol, tertatolol, oxprenolol, amusolalul, carvedilol, labetalol, S-atenolol, OPC-1085, quinapril, lisinopril, enalapril, captopril, benazepril, perindopril, trandolapril, fosinopril, ramipril, cilazapril, delapril, imidapril, moexipril, spirapril, temocapril, zofenopril, S-5590, fasidotril, Hoechst-Marion Roussel: 100240 (EP00481522), omapatrilat, gemopatrilat and GW-660511, nifedipine, felodipine, nicardipine, isradipine, nimodipine, diltiazem, amlodipine, nitrendipine, verapamil, lacidipine, lercanidipine, aranidipine, cilnidipine, clevidipine, azelnidipine, barnidipine, efonodipine, iasidipine, iemildipine, iercanidipine, manidipine, nilvadipine, pranidipine, furnidipine, doxazosin, urapidil, prazosin, terazosin, bunazosin and OPC-28326, bendroflumetazide, chlorothalidone, hydrochlorothiazide and clopamide, bumetanide, furosemide, torasemide, amiloride, spironolactone, ABT-546, ambrisetan, atrasentan, SB-234551, CI-1034, S-0139, YM-598, bosentan, J-104133, aliskiren, OPC-21268, tolvaptan, SR-121463, OPC-31260, Nesiritide, irbesartan, candesartancilexetil, losartan, valsartan, telmisartan, eprosartan, candesartan, CL-329167, eprosartan, iosartan, olmesartan, pratosartan, TA-606, YM-358, fenoldopam, ketanserin, naftopidil, N-0861, FK-352, KT2-962, ecadotril, LP-805, MYD-37, nolomirole, omacor, treprostinil, beraprost, ecraprost, PST-2238, KR-30450, PMD-3117, Indapamides, CGRP-unigene, guanylate cyclase stimulators, hydralazines, methyldopa, docarpamine, moxonidine, CoAprovel, and MondoBiotech-811. In said aspect of the invention a pharmaceutical composition which, comprises the combination of a 11β-HSD1 inhibitor of the present invention and an antihypertensive agent, is provided.

PCT International application WO 2004/089415 provides the benefits of a combination therapy comprising the administration of a 11β-HSD1 inhibitor and a glucocorticoid receptor agonist for the reduction of undesirable side effects occurring during glucocorticoid receptor agonist therapy and for treating some forms of cancer, diseases and disorders having inflammation as a component. In particular in reducing the adverse effects of glucocorticoid receptor agonist therapy in indications of Cushing's disease, Cushing's syndrome, allergic-inflammatory diseases, adverse effects of glucocorticoid receptor agonist treatment of disorders of the respiratory system, adverse effects of glucocorticoid receptor agonist treatment of inflammatory bowel disease; adverse effects of glucocorticoid receptor agonist treatment of disorders of the immune system, connective tissue and joints; adverse effects of glucocorticoid receptor agonist treatment of endocrinological diseases; adverse effects of glucocorticoid receptor agonist treatment of hematological diseases; adverse effects of glucocorticoid receptor agonist treatment of cancer, chemotherapy-induced nausea, adverse effects of glucocorticoid receptor agonist treatment of diseases of muscle and at the neuro-muscular joint; adverse effects of glucocorticoid receptor agonist treatment in the context of surgery8; transplantation; adverse effects of glucocorticoid receptor agonist treatment of brain abscess, nausea/vomiting, infections, hypercalcemia, adrenal hyperplasia, autoimmune hepatitis, spinal cord diseases, saccular aneurysms.

Examples for the indications wherein a combination of a 11β-HSD1 compound of the present invention with a glucocorticoid receptor agonists may be beneficial are: Cushing's disease, Cushing's syndrome, asthma, atopic dermatitis, cystic fibrosis, emphysema, bronchitis, hypersensitivity, pneumonitis, eosinophilic pneumonias, pulmonary fibrosis, Crohn's disease, Ulcerative colitis, reactive arthritis, rheumatoid arthritis, Sjogren's syndrome, systemic lupus erythematosus, lupus nephritis, Henoch-Schnlein purpura, Wegener's granulomatosis, temporal arteritis, systemic sclerosis, vasculitis, sarcoidosis, dermatomyositis-polymyositis, pemphigus vulgaris, hyperthyroidism, hypoaldosteronism, hypopituitarism, hemolytic anemia, thrombocytopenia, paroxysmal nocturnal hemoglobinuria, neoplastic compression of the spinal cord, brain tumours, acutelymphoblastic leukemia, Hodgkin's disease, chemotherapy-induced nausea, myasthenia gravis, heriditary myopathies, Duchenne muscular dystrophy, trauma, post-surgical stress, surgical stress, renal transplantation, liver transplantation, lung transplantation, pancreatic islet transplantation, blood stem cell transplantation, bone marrow transplantation, heart transplantation, adrenal gland transplantation, trachea transplantation, intestinal transplantation, corneal transplantation, skin grafting, keratoplasty, lens implantation, brain abscess, nausea/vomiting, infections, hypercalcemia, adrenal hyperplasia, autoimmune hepatitis, spinal cord diseases, and saccular aneurysms. It is accordingly an object of the present invention to provide any of the aforementioned group of compounds in a combination therapy with a glucocorticoid receptor agonist, as well as pharmaceutical formulations comprising said combination of a compound of the present invention with a glucocorticoid receptor agonist. The glucocorticoid receptor agonist is, for example, selected from the group consisting of: betamethasone, dexamethasone, hydrocortisone, methylprednisolone, prednisolone, prednisone, beclomethasone, butixicort, clobetasol, flunisolide, flucatisone (and analogues), mometasone, triamcinolonacetonide, triamcinolonhexacetonide GW-685698, NXC-1015, NXC-1020, NXC-1021, NS-126, P-4112, P-4114, RU-24858 and T-25 series.

In order to simplify the representation of the compounds of formula (I) the group

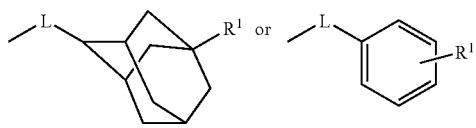

will hereinafter being referred to as -D.

The "curved" tricyclic adamantylamide derivatives of the present invention, hereinafter referred to as the compounds of formula (I'), are generally prepared by condensing in a first step the commercially available benzocyclobutane carboxylic acid (II) with the appropriate amine under art known conditions (Scheme 1). Subsequently, the thus obtained amide (III) is reduced using for example, lithium aluminium hydride or borane dimethyl sulphide complex, to give the amine of formula (IV). Finally, said amine is acylated with acroyl chloride followed by a cyclisation reaction, under art known procedures, such as for example by heating the amide (V) in toluene at 190° C., to yield a mixture of the cis and trans isomers of the "curved" tricyclic adamantylamide derivatives of the present invention.

To obtain the stereoisomers of the "curved" tricyclic adamantylamide derivatives of formula (I') hereinbefore, the commercially available benzocyclobutane carboxylic acid (II) is condensed with allyl-2-adamantyl-amine (VI) to yield the amide of general formula (VII), which upon electrocyclic ring closure afforded the "curved" tricyclic adamantylamide derivatives of formula (I'') (Scheme 2).

Scheme 2

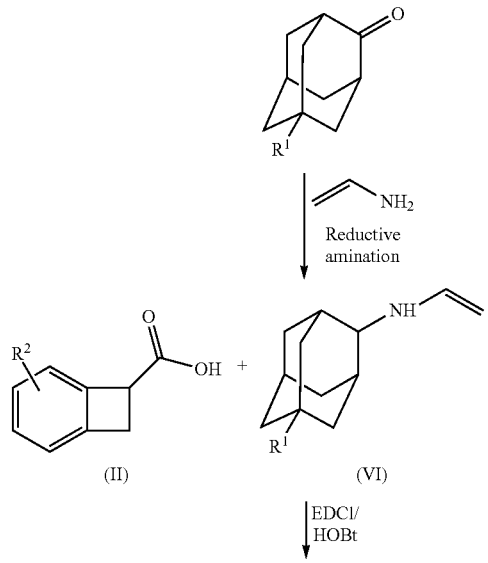

Scheme 1

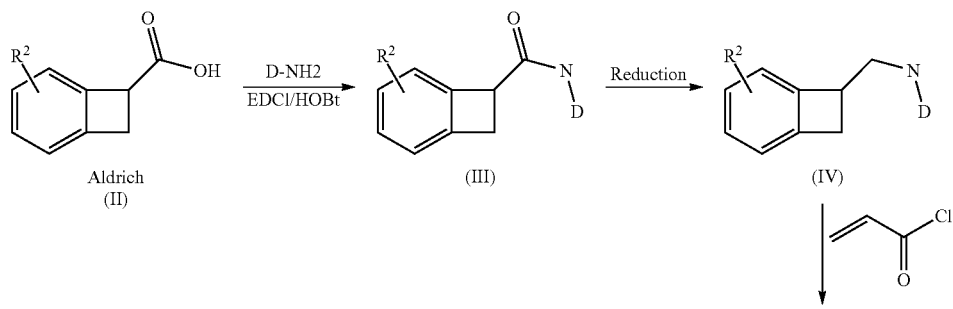

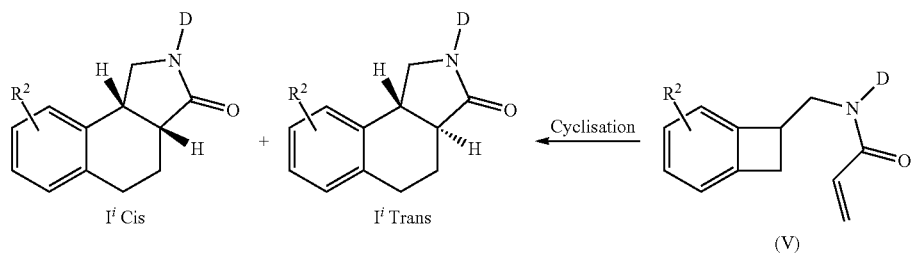

wherein $R^2$ is defined as for the compounds of formula (I) hereinbefore.

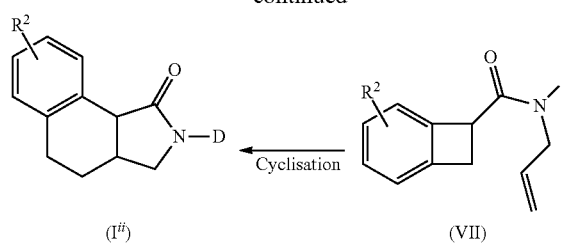

wherein $R^1$ and $R^2$ are defined as for the compounds of formula (I) hereinbefore.

Those compounds of formula (I) wherein X represents N, hereinafter referred to as the ureas of formula (I$^{iii}$) are generally prepared according to reaction schemes 3 and 4 hereinafter. In a first alternative, the ureas are prepared starting from commercially available Boc-protected tetrahydroquinoline-3-carboxylic acid (both enantiomers), reaction with aminoadamantane and reduction of the amide gave the diamine of formula (VIII). Subsequent cyclization under art known procedures gave the cyclic ureas of formula (I$^{iii}$).

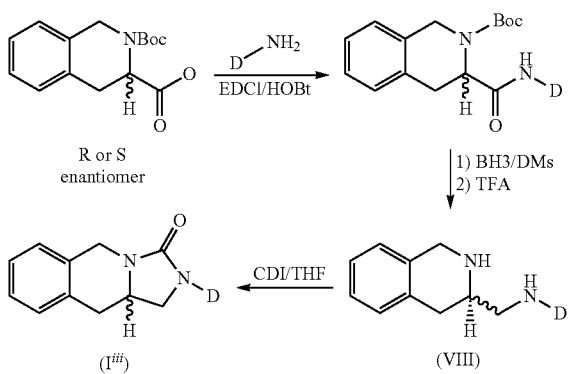

In a second alternative the urea derivatives are prepared by coupling the commercially available quinoline-2-carboxylic acids or isoquinoline-1-carboxylic acids with the appropriate amine under art known procedures to yield the corresponding amide of formula (IX). Selective hydrogenation of the pyridine ring afforded the tetrahydro(iso)quinolines acetamides (X), which were reduced using for example, BH3.DMS in toluene to yield the diamines of general formula (XI). Subsequent cyclization, using for example carbonyl diimidazole (CDI) gave the cyclic ureas of formula (I$^{iii}$).

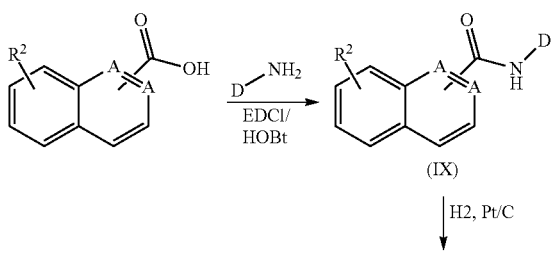

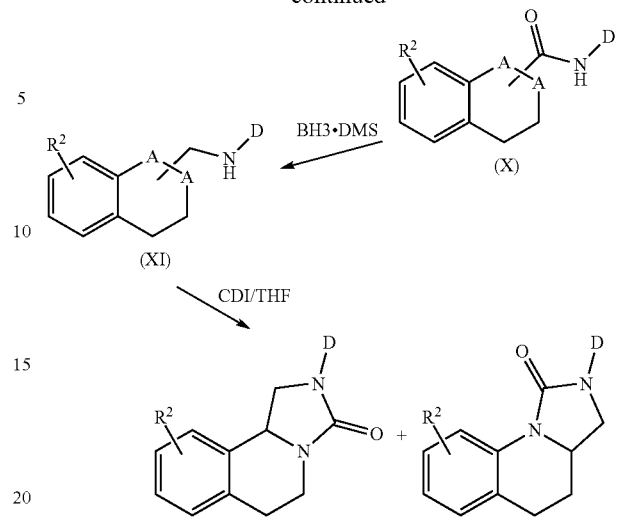

wherein $R^2$ is defined as for the compounds of formula (I) hereinbefore, -A-A- represents —N—CH$_2$— or —CH$_2$—N— and -A=A- represents —N=CH— or —CH=N—.

In those cases where the substituted isoquinoline-1-carboxylic acids were not commercially available, the substituted tricyclic derivatives were built up starting from phenethylamines (XII) and ethylchloroformate (Scheme 5). The created carbamate was cyclized using art known procedures, such as for example the modified Bischler-Napierelski reaction (Larsen, Robert D., et al., A modified Bischler-Napieralski procedure for the synthesis of 3-aryl-3,4-dihydroisoquinolines, Journal of Organic Chemistry (1991), 56(21), 6034-8.), to give the amino protected tetrahydroisoquinoline-1-carboxylic acid of formula (X'). The further synthesis of the substituted tricyclic derivatives is as described in reaction Scheme 4 hereinbefore.

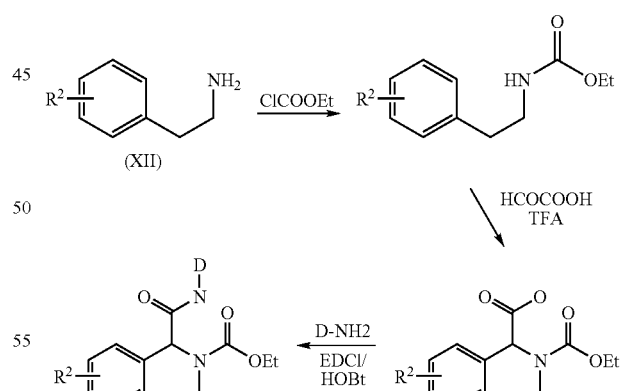

The "linear" tricyclic adamantylamide derivatives of formula (I$^{iv}$) can be prepared according to reaction schemes 6 and 7 herein after. According to a first alternative the linear tricyclic adamantylamide derivatives are prepared starting from the aryl- or heteroaryl-substituted acrylic acid or acid chloride (XIII). Reaction with the appropriate amine gives the amide of formula (XIV), which upon electrocyclic ring closure under art known conditions, for example in toluene at 220° C., provides the tricyclic system of formula (I$^{iv}$).

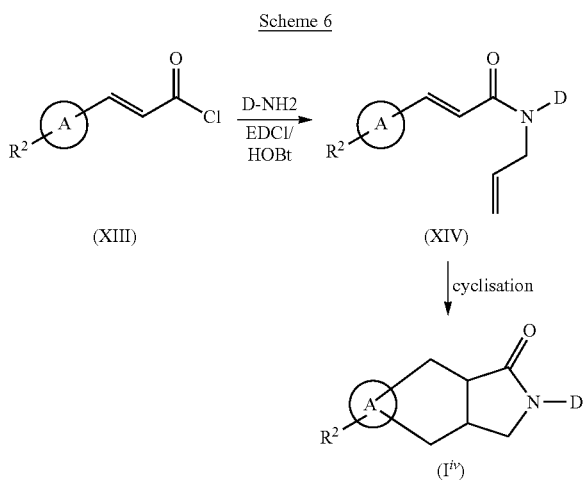

wherein A and R$^2$ are defined as for the compounds of formula (I) hereinbefore.

In a second alternative the "linear" tricyclic adamantylamide derivatives of formula (I$^{iv}$) wherein A represents phenyl and Y represents N, can be prepared by coupling the amino protected D or L-phenylalanine with the appropriate amine to give the α-aminoamide of formula (XV), see for example the reaction conditions as described in J. Org. Chem. 2002, 67, 8224. Deprotection followed by Mannich condensation with benzotriazole and formaldehyde provides the intermediate of formula (XVI). Electrocyclic ring closure provides the "linear" tricyclic adamantylamide derivatives of formula (I$^{iv}$).

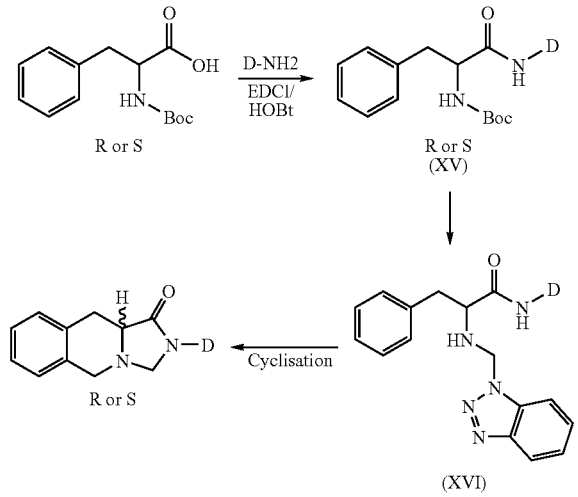

Further examples for the synthesis of compounds of formula (I) using anyone of the above-mentioned synthesis methods, are provided in the experimental part hereinafter.

Where necessary or desired, any one or more of the following further steps in any order may be performed:
(i) removing any remaining protecting group(s);
(ii) converting a compound of formula (I) or a protected form thereof into a further compound of formula (I) or a protected form thereof;
(iii) converting a compound of formula (I) or a protected form thereof into a N-oxide, a salt, a quaternary amine or a solvate of a compound of formula (I) or a protected form thereof;
(iv) converting a N-oxide, a salt, a quaternary amine or a solvate of a compound of formula (I) or a protected form thereof into a compound of formula (I) or a protected form thereof;
(v) converting a N-oxide, a salt, a quaternary amine or a solvate of a compound of formula (I) or a protected form thereof into another N-oxide, a pharmaceutically acceptable addition salt a quaternary amine or a solvate of a compound of formula (I) or a protected form thereof;
(vi) where the compound of formula (I) is obtained as a mixture of (R) and (S) enantiomers resolving the mixture to obtain the desired enantiomer.

It will be appreciated by those skilled in the art that in the processes described above the functional groups of intermediate compounds may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include C$_{(1-6)}$ alkyl or benzyl esters.

The protection and deprotection of functional groups may take place before or after a reaction step.

The use of protecting groups is fully described in 'Protective Groups in Organic Synthesis' 2$^{nd}$ edition, T W Greene & P G M Wutz, Wiley Interscience (1991).

Additionally, the N-atoms in compounds of formula (I) can be methylated by art-known methods using CH$_3$—I in a suitable solvent such as, for example 2-propanone, tetrahydrofuran or dimethylformamide.

The compounds of formula (I), can also be converted into each other following art-known procedures of functional group transformation of which some examples are mentioned hereinabove.

The compounds of formula (I), may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I), may be obtained by the application of art-known procedures. Diastereomers may be separated by physical methods such as selective crystallization and chromatographic techniques, e.g. counter-current distribution, liquid chromatography and the like.

Some of the compounds of formula (I), and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures.

The compounds of the present invention are useful because they possess pharmacological properties. They can therefore be used as medicines, in particular to treat pathologies associated with excess cortisol formation, i.e. disorders where a decreased level of active glucocorticoid is desirable, such as metabolic syndrome, type 2 diabetes, impaired glucose tolerance (IGT), impaired fasting glucose (IFG), dyslipidemia, hypertension, obesity, diabetes, obesity related cardiovascular diseases, arteriosclerosis, atherosclerosis, myopathy, osteoporosis, neurodegenerative and psychiatric disorders, stress related disorders and glaucoma. In particular to treat pathologies such as for example, obesity, diabetes, type 2 diabetes, obesity related cardiovascular diseases, stress and glaucoma.

As described in the experimental part hereinafter, the inhibitory effect of the present compounds on the 11β-HSD1-reductase activity (conversion of cortisone into cortisol) has been demonstrated in vitro, in an enzymatic assay using the recombinant 11b-HSD1 enzyme, by measuring the conversion of cortisone into cortisol using HPLC purification and quantification methods. 11β-HSD1-reductase inhibition was also demonstrated in vitro, in a cell based assay comprising contacting the cells, expressing 11β-HSD1 with the compounds to be tested and assessing the effect of said compounds on the formation of cortisol in the cellular medium of these cells. The cells preferably used in an assay of the present invention are selected from the group consisting of mouse fibroblast 3T3-L1 cells, HepG2 cells, pig kidney cell, in particular LCC-PK1 cells and rat hepatocytes.

Accordingly, the present invention provides the compounds of formula (I) and their pharmaceutically acceptable N-oxides, addition salts, quaternary amines and stereochemically isomeric forms for use in therapy. In particular to treat pathologies associated with excess cortisol formation, i.e. disorders where a decreased level of active glucocorticoid is desirable, such as metabolic syndrome, type 2 diabetes, impaired glucose tolerance (IGT), impaired fasting glucose (IFG), dyslipidemia, hypertension, obesity, diabetes, obesity related cardiovascular diseases, arteriosclerosis, atherosclerosis, myopathy, osteoporosis, neurodegenerative and psychiatric disorders, stress related disorders and glaucoma. More particular to treat pathologies such as for example, obesity, diabetes, type 2 diabetes, obesity related cardiovascular diseases, stress and glaucoma. Even more particular in the treatment or prevention of pathologies associated with excess cortisol formation such as obesity, diabetes, obesity related cardiovascular diseases and glaucoma.

In view of the utility of the compounds according to the invention, there is provided a method for the treatment of an animal, for example, a mammal including humans, suffering from a pathology associated with excess cortisol formation, which comprises administering an effective amount of a compound according to the present invention. Said method comprising the systemic or topical administration of an effective amount of a compound according to the invention, to warm-blooded animals, including humans.

It is thus an object of the present invention to provide a compound according to the present invention for use as a medicine. In particular to use the compound according to the present invention in the manufacture of a medicament for treating pathologies associated with excess cortisol formation such as for example, metabolic syndrome, type 2 diabetes, impaired glucose tolerance (IGT), impaired fasting glucose (IFG), dyslipidemia, hypertension, obesity, diabetes, obesity related cardiovascular diseases, arteriosclerosis, atherosclerosis, myopathy, osteoporosis, neurodegenerative and psychiatric disorders, stress related disorders and glaucoma, in particular obesity, diabetes, obesity related cardiovascular diseases, stress and glaucoma.

The amount of a compound according to the present invention, also referred to here as the active ingredient, which is required to achieve a therapeutical effect will be, of course, vary with the particular compound, the route of administration, the age and condition of the recipient, and the particular disorder or disease being treated. A suitable daily dose would be from 0.001 mg/kg to 500 mg/kg body weight, in particular from 0.005 mg/kg to 100 mg/kg body weight. A method of treatment may also include administering the active ingredient on a regimen of between one and four intakes per day.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous, or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellant such as nitrogen, carbon dioxide, a freon, or without a propellant such as a pump spray, drops, lotions, or a semisolid such as a thickened composition which can be applied by a swab. In particular, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In order to enhance the solubility and/or the stability of the compounds of formula (I) in pharmaceutical compositions, it can be advantageous to employ α-, β- or γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

EXPERIMENTAL PART

In the procedures described hereinafter the following abbreviations were used: "THF", which stands for tetrahydrofuran; "DIPE" stands for diisopropylether; "EtOAc" stands for ethyl acetate; "DMF" stands for N,N-dimethylformamide, "BMS" stands for trihydro[thiobis[methane]]boron [13292-87-0].

Extrelut™ is a product of Merck KgaA (Darmstadt, Germany) and is a short column comprising diatomaceous earth. Supelco is a prepacked silicagel liquid chromatography column.

For some chemicals the chemical formula was used, e.g. $CH_2Cl_2$ for dichloromethane, $CH_3OH$ for methanol, HCl for hydrochloric acid, KOH for potassium hydroxide, NaOH for sodium hydroxide, $Na_2CO_3$ for sodium carbonate, $NaHCO_3$ for sodium hydrogen carbonate, $MgSO_4$ for magnesium sulfate, $N_2$ for nitrogen gas, $CF_3COOH$ for trifluoroacetic acid.

A. Preparation of the Intermediates

Example A1

Preparation of

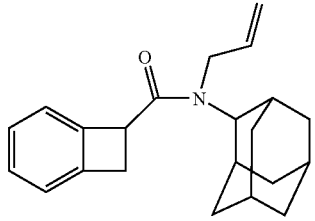

intermediate 1

Thionyl chloride (0.5 ml) was added to a solution of bicyclo[4.2.0]octa-1,3,5-triene-7-carboxylic acid [14381-41-0] (0.001 mol) in dichloromethane. The reaction mixture was refluxed for 1 hour. Then stirred overnight at room temperature. The solvents were co-evaporated 2 times with benzene to obtain bicyclo[4.2.0]octa-1,3,5-triene-7-carbonyl chloride [1473-47-8] which was dissolved in DIPE. The obtained solution was added dropwise to a cooled mixture (0° C.) of N-allyl-2-adamantanamine [24161-63-5] and sodium carbonate in DIPE. The reaction mixture was stirred for 30 minutes on ice and then for 2 hours at room temperature. The mixture was poured out into water and extracted with dichloromethane. The organic layer was filtered through Extrelut™ and the filtrate was evaporated. The residue was purified by flash column chromatography on TRIKONEX FlashTube™ (eluent: $CH_2Cl_2$/EtOAc 90/10). The product fractions were collected and the solvents were evaporated, yielding 0.13 g of intermediate 1.

Example A2 a) Preparation of

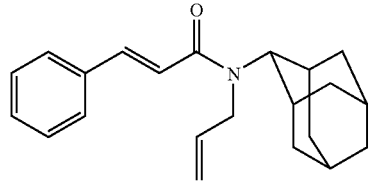

intermediate 2

A mixture of 3-phenyl-2-propenoic acid [140-10-3] (0.01 mol) and thionyl chloride (30 ml) was refluxed for 2 hours. The solvent was co-evaporated with methylbenzene. The residue was dissolved in DIPE (20 ml) and the resulting solution was added dropwise to a mixture of N-allyl-2-adamantanamine [24161-63-5] (0.01 mol) and sodium carbonate (2 g) in DIPE (50 ml) on ice. The reaction mixture was stirred overnight, poured out into dichloromethane and washed with water. The organic layer was separated, dried (MgSO$_4$), filtered and the solvent was evaporated. The residue was purified by column chromatography over silica gel (eluent: CH$_2$Cl$_2$). The product fractions were collected and the solvent was evaporated. The residue was triturated under DIPE and the desired product was collected, yielding 1.68 g (56%) of intermediate 2.

Example A3 a) Preparation of

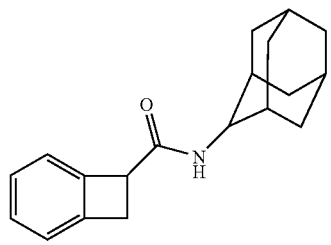

intermediate 3

A solution of bicyclo[4.2.0]octa-1,3,5-triene-7-carboxylic acid [14381-41-0] (0.0033 mol) in dichloromethane (25 ml) and N,N-diethylethanamine (5 ml) was stirred and 1-hydroxy-1H-benzotriazole (0.0035 mol) was added. Then N'-(ethylcarbonimidoyl)-N,N-dimethyl-1,3-propanediamine, monohydrochloride (0.0035 mol) was added and the mixture was stirred for 10 minutes. Tricyclo[3.3.1.13,7]decan-2-amine, hydrochloride (1:1) [10523-68-9] (0.0035 mol) was added and the reaction mixture was stirred for 2 days. The mixture was washed with a 15% citric acid solution and with a sodium carbonate solution. The organic layer was separated, dried, filtered and the solvent was evaporated. The residue was triturated with DIPE and the desired product was collected, yielding 0.6 g of intermediate 3.

b) Preparation of

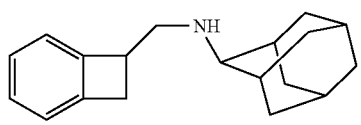

intermediate 4

Lithium Aluminum hydride (0.0042 mol) was stirred in diethyl ether (10 ml) (on ice) and Aluminum chloride (0.0042 mol) was added, the mixture was stirred for 15 minutes and intermediate 3 (0.0021 mol) was added portionwise. The reaction mixture was stirred at room temperature for 2 hours and then quenched with a diluted HCl solution. A diluted KOH solution was added until pH 10 and the resulting mixture was extracted with dichloromethane. The organic layer was separated and dried, then filtered through Extrelut™ and the filtrate was evaporated, yielding 0.489 g of intermediate 4.

c) Preparation of

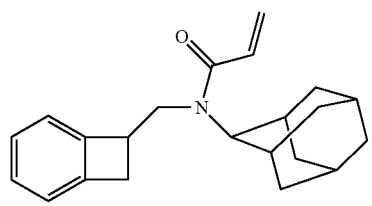

intermediate 5

A mixture of intermediate 4 (0.0018 mol) and sodium carbonate (0.3 g) in dichloromethane (10 ml) was stirred on ice. 2-Propenoyl chloride [814-68-6] (0.002 mol) was added dropwise and the reaction mixture was stirred overnight at room temperature. The mixture was washed with water (4 ml) and filtered through Extrelut and the filtrate was evaporated, yielding 0.497 g of intermediate 5.

Example A4 a) Preparation of

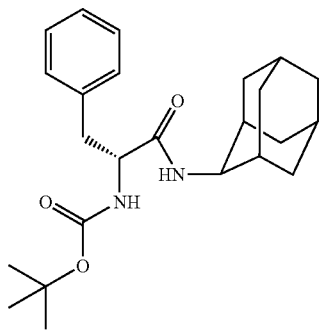

intermediate 6

1-Hydroxy-1H-benzotriazole (0.02 mol) was added to a mixture of N-[(1,1-dimethylethoxy)carbonyl]-D-phenylalanine [18942-49-9] (0.0075 mol) and N,N-diethylethanamine (5 ml) in dichloromethane (100 ml). After 5 minutes stirring N'-(ethylcarbonimidoyl)-N,N-dimethyl-, 1,3-propanediamine, monohydrochloride [25952-53-8] (0.02 mol) was added. After stirring for 10 minutes, tricyclo[3.3.1.13,7]decan-2-amine, hydrochloride [10523-68-9] (0.015 mol) was added and the reaction mixture was stirred overnight at room temperature. The mixture was poured out into water and extracted with dichloromethane. The organic layer was dried, filtered and the solvent was evaporated, yielding 2.5 g of intermediate 6.

b) Preparation of

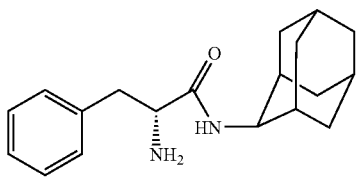

intermediate 7

A mixture of intermediate 6 (0.0075 mol) in dichloromethane (50 ml) and trifluoroacetic acid (10 ml) was stirred overnight and the solvents were evaporated. The residue was dissolved in dichloromethane and washed with a sodium carbonate solution. The organic layer was dried, filtered and the solvent was evaporated. The residue was triturated with DIPE and the desired product was collected, yielding 1.4 g of intermediate 7.

c) Preparation of intermediate 8

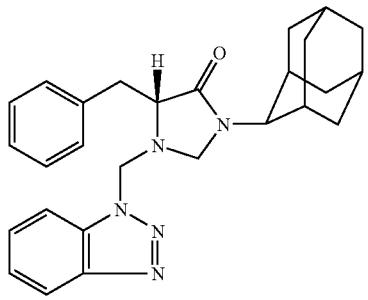

A mixture of intermediate 7 (0.0046 mol), 1H-benzotriazole [95-14-7] (0.0092 mol), paraformaldehyde (0.0138 mol) and 4-methylbenzenesulfonic acid [104-15-4] (0.18 g) in benzene (60 ml) was refluxed over a Dean-Starck setting for 3 hours. Then stirred overnight at room temperature. The solvent was evaporated, toluene (60 ml) was added and the mixture was refluxed over a Dean-Starck setting for next 2 hours. The mixture was cooled and washed with a NaOH-solution (2M). The organic layer was dried over $MgSO_4$, filtered and the solvent was evaporated, yielding 2.3 g of intermediate 8.

Example A5 a) Preparation of intermediate 9

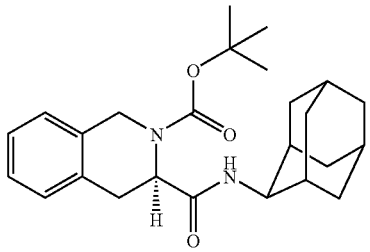

1-Hydroxy-1H-benzotriazole (0.0012 mol) and N-(ethylcarbonimidoyl)-N,N-dimethyl-1,3-propanediamine, monohydrochloride [25952-53-8] (0.0012 mol) were added to a mixture of (3R)-3,4-dihydro-2,3(1H)-isoquinolinedicarboxylic acid, 2-(1,1-dimethylethyl) ester [115962-35-1] (0.001 mol) in DMF (10 ml) and N,N-diethylethanamine (0.2 ml). The mixture was stirred for 20 minutes at room temperature. Tricyclo[3.3.1.13,7]decan-2-amine, hydrochloride [10523-68-9] (0.0012 mol) was added and the reaction mixture was stirred overnight. The mixture was poured out into water and stirred for 10 minutes, then the resulting precipitate was filtered off and dissolved in dichloromethane. The obtained solution was washed with water, dried over $MgSO_4$, filtered and the solvent was evaporated, yielding 0.38 g of intermediate 9.

b) Preparation of intermediate 10

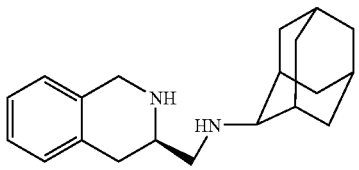

A mixture of intermediate 9 (0.00087 mol) in toluene (10 ml) was stirred on ice (under $N_2$). BMS (0.001 mol) was added dropwise, then the reaction mixture was stirred on ice for 30 minutes. The mixture was refluxed overnight. The mixture was cooled and washed with a $Na_2CO_3$-solution. The organic solvent was evaporated. The residue was dissolved in $CH_2Cl_2/CF_3COOH$ (20%) and stirred for 20 hours at room temperature. The solvents were evaporated. The residue was dissolved in $CH_2Cl_2$, and washed with a $Na_2CO_3$ solution. The organic layer was concentrated and the residue was purified over Supelco column filled by silica gel (eluent: $CH_2Cl_2/CH_3OH$ gradient). The product fractions were collected and the solvents were evaporated, yielding 0.120 g of intermediate 10.

Example A6 a) Preparation of intermediate 11

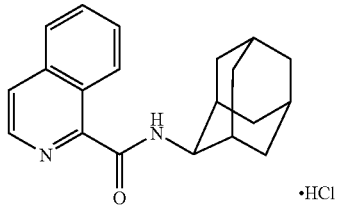

To a stirred solution of 1-isoquinolinecarboxylic acid (0.0056 mol) and N,N-diethylethanamine (0.7 g) in DMF (50 ml) were added 1-hydroxy-1H-benzotriazole (0.0067 mol) and N-(ethylcarbonimidoyl)-N,N-dimethyl-1,3-propanediamine, monohydrochloride [25952-53-8] (0.0067 mol). The mixture was stirred for 20 minutes at room temperature. Tricyclo[3.3.1.1³,⁷]decan-2-amine, hydrochloride [10523-68-9] (0.0067 mol) was added and the reaction mixture was stirred overnight. The mixture was poured out into water, stirred for 10 minutes and extracted with dichloromethane. The organic layer was separated, dried over MgSO₄, filtered and the solvent was evaporated. The residue was dissolved in 2-propanol and converted into the hydrochloric acid salt (1:1) with HCl/2-propanol. The desired product was filtered, yielding 1.2 g of intermediate 11.

b) Preparation of

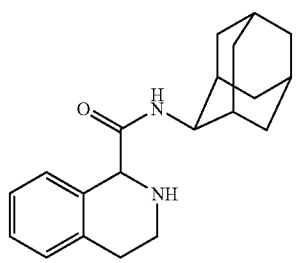

intermediate 12

A solution of intermediate 11 (0.0035 mol) in HCl, 2-propanol (1 ml) and methanol (50 ml) was hydrogenated overnight with platinum on activated carbon (0.5 g) as a catalyst. After uptake of hydrogen (2 equiv.), the catalyst was filtered off and the filtrate was evaporated. The residue was dissolved in dichloromethane and washed with a Na₂CO₃-solution. The organic layer was separated, dried (MgSO₄), filtered and the solvent was evaporated. The residue was purified on Supelco column filled by silica gel (eluent: CH₂Cl₂/CH₃OH 99/1). Two product fractions were collected and the solvent was evaporated, yielding 0.370 g of intermediate 12.

c) Preparation of

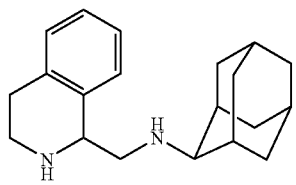

intermediate 13

A solution of intermediate 12 (0.0012 mol) in toluene (10 ml) was stirred on ice (N₂). BMS (0.002 mol) was added dropwise, then the reaction mixture was stirred on ice for 30 minutes and stirred overnight at 100° C. The mixture was washed with a NaHCO₃ solution and extracted with CH₂Cl₂. The organic layer was separated, dried (MgSO₄), filtered and the solvent was evaporated, yielding 0.29 g of residue. The residue was triturated with DIPE and the precipitate was filtered. The filtrate was evaporated, yielding 0.22 g of intermediate 13.

Example A7 a) Preparation of

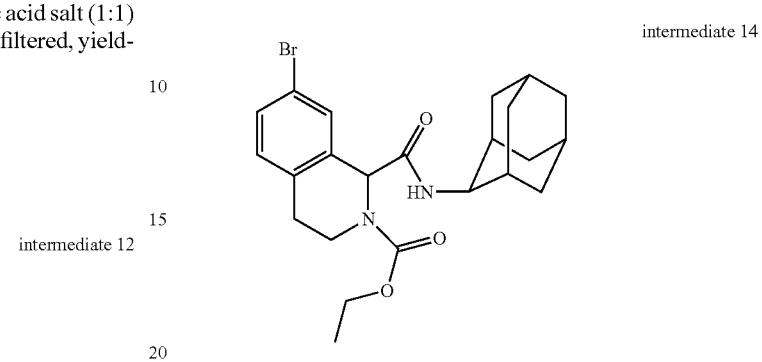

intermediate 14

A mixture of 7-bromo-3,4-dihydro-1,2(1H)-isoquinolinedicarboxylic acid, 2-ethyl ester [135335-12-5] (0.006 mol) and N,N-diethylethanamine (5 ml) in DMF (40 ml) was stirred and 1-hydroxy-1H-benzotriazole (0.0067 mol) was added. Then N'-(ethylcarbonimidoyl)-N,N-dimethyl-1,3-propanediamine, monohydrochloride [25952-53-8] (0.0067 mol) was added and the mixture was stirred for 20 minutes. Tricyclo[3.3.1.1³,⁷]decan-2-amine, hydrochloride [10523-68-9] (0.0067 mol) was added and the reaction mixture was stirred overnight at room temperature. The mixture was poured out into water, stirred for 10 minutes. The resulting precipitate was filtered, dissolved in CH₂Cl₂, dried over MgSO₄, filtered and the solvent was evaporated. The residue was triturated with DIPE and the desired product was collected, yielding 1.6 g of intermediate 14.

b) Preparation of

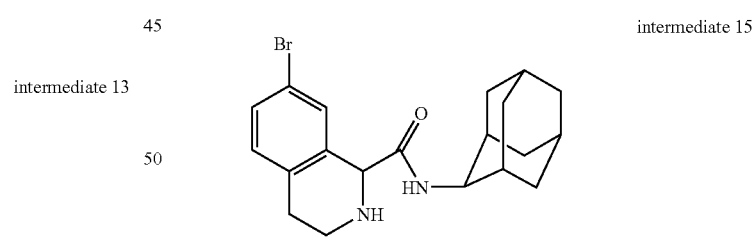

intermediate 15

A solution of intermediate 14 (0.0034 mol) in a HBr/CH₃COOH mixture (50 ml) was stirred at room temperature for 1 week. The mixture was poured out into water and stirred for 15 minutes. The precipitate was filtered and dissolved in CH₂Cl₂. The solution was washed with a NaHCO₃-solution, dried (MgSO₄), filtered and the solvent was evaporated. The residue was triturated under DIPE and the desired fraction was collected (yielding 0.7 g). This fraction was dissolved in diluted HCl and the resulting solution was washed with CH₂Cl₂. The aqueous layer was alkalised with a Na₂CO₃ solution and extracted with CH₂Cl₂. The organic layer was separated, dried (MgSO$_4$), filtered and the solvent was evaporated, yielding 0.35 g of intermediate 15.

c) Preparation of

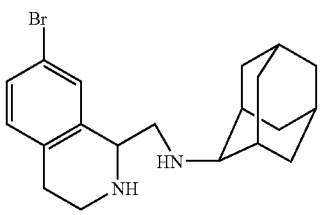

intermediate 16

A mixture of intermediate 15 (0.00089 mol) in toluene (50 ml) and THF (20 ml) was stirred under N$_2$ until complete dissolution and then the solution was stirred under N$_2$ on ice. BMS (0.002 mol) was added dropwise and the reaction mixture was stirred for 30 minutes under N$_2$ on ice. The mixture was further stirred overnight at 100° C. and was then cooled. 1N HCl (50 ml) was added. The mixture was stirred and refluxed for 2 hours. The resulting mixture was cooled, neutralised with a Na$_2$CO$_3$ solution and extracted with CH$_2$Cl$_2$. The organic layer was separated, dried (MgSO$_4$), filtered and the solvent was evaporated, yielding 0.3 g of intermediate 16.

B. Preparation of the Compounds

Example B1

Preparation of

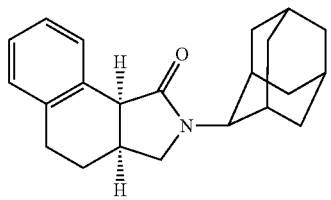

compound 1

A mixture of intermediate 1 (0.00093 mol) in anhydrous methylbenzene (10 ml) was stirred for 6 hours at 190° C. and then stirred overnight at room temperature. The solvent was evaporated and the residue was purified by column chromatography over silica gel (eluent: CH$_2$Cl$_2$). The product fractions were collected and the solvent was evaporated, yielding 0.19 g (63%) of compound 1.

Example B2

Preparation of

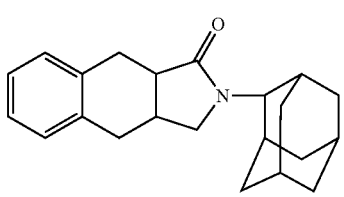

compound 2

A mixture of intermediate 2 (0.00031 mol) and 4-methoxyphenol (catalytic quantity) in methylbenzene (10 ml) was stirred for one hour at 220° C. The solvent was evaporated. The residue was purified (2×) by flash column chromatography on TRIKONEX FlashTube™ (eluent: CH$_2$Cl$_2$/EtOAc 90/10). The product fractions were collected to give 0.008 g of compound 2.

Example B3

Preparation of

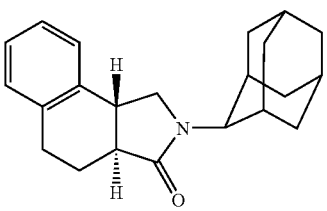

compound 3

A solution of intermediate 5 (0.0015 mol) in methylbenzene (15 ml) was stirred in pressure vessel at 190° C. for 6 hours. Then the reaction mixture was stirred overnight at room temperature. The solvent was evaporated and the residue was purified on Supelco column filled with silica gel (eluent: CH$_2$Cl$_2$). Fractions were collected and the solvent was evaporated, yielding 0.1 g of compound 3.

Example B4

Preparation of

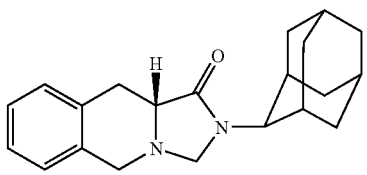

compound 4

Intermediate 8 (0.006 mol) in dichloromethane (250 ml) was stirred and aluminum chloride (0.018 mol) was added. The reaction mixture was refluxed for 3 hours. The mixture was cooled and washed with KOH (1M). The organic layer was washed, dried, filtered and the solvent was evaporated, yielding 0.7 g of residue. A part (0.3 g) of the residue was purified over silica gel (eluent: CH$_2$Cl$_2$/EtOAc 90/10). The product fractions were collected and the solvent was evaporated, yielding 0.133 g of compound 4.

Example B5

Preparation of

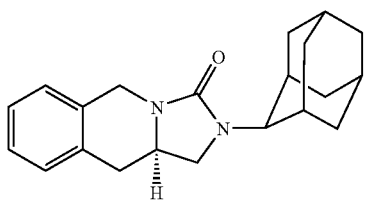

compound 5

A solution of intermediate 10 (0.00040 mol) in tetrahydrofuran (10 ml) was stirred and 1,1'-carbonylbis-1H-imidazole [530-62-1] (0.00045 mol) was added. The mixture was refluxed overnight. After cooling, water (2 ml) was added. The mixture was extracted with dichloromethane and the organic layer was filtered through Extrelut™. The obtained residue was purified by column chromatography over silica gel (Supelco) (eluent: $CH_2Cl_2$). The product fractions were collected and the solvent was evaporated, yielding 0.063 g of compound 5.

Example B6

Preparation of

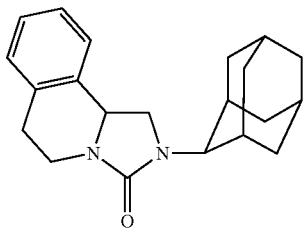

compound 6

1,1'-Carbonylbis-1H-imidazole [530-62-1] (0.00185 mol) was added to a stirred solution of intermediate 13 (0.00048 mol) in tetrahydrofuran (15 ml). The reaction mixture was stirred for 48 hours at 60° C. and cooled. Water (4 ml) was added. The mixture was stirred for 10 minutes and extracted with dichloromethane (10 ml). The organic layer was separated, dried ($MgSO_4$), filtered and the solvent was evaporated. The residue (0.337 g) was purified 2 times on Supelco column filled by silica gel (eluent: $CH_2Cl_2$). The product fractions were collected and the solvent was evaporated, yielding 0.051 g of compound 6.

Example B7

Preparation of

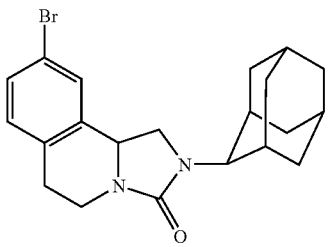

compound 7

A mixture of intermediate 16 (0.0008 mol) in tetrahydrofuran (5 ml) was stirred and 1,1'-carbonylbis-1H-imidazole (0.5 g) was added. The reaction mixture was stirred overnight at room temperature and the solvent was evaporated. The residue was purified by column chromatography (Supelco) over silica gel (eluent: $CH_2Cl_2$/EtOAc 90/10). The product fractions were collected and the solvents were evaporated, yielding 0.068 g of compound 7.

Table F-1 lists the compounds that were prepared according to one of the above Examples.

TABLE F-1

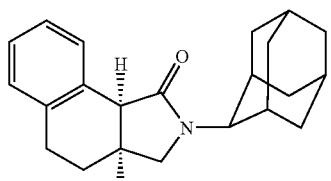

Co. No. 1; Ex. B1.

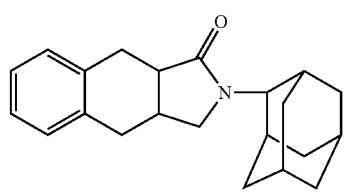

Co. No. 2; Ex. B2.

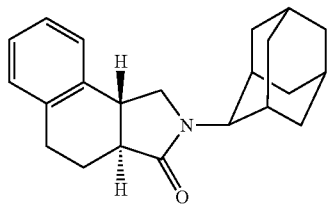

Co. No. 3; Ex. B3.

TABLE F-1-continued
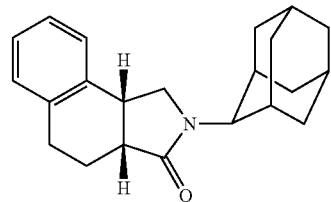
Co. No. 8; Ex. B3.
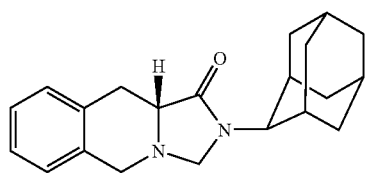
Co. No. 4; Ex. B4.
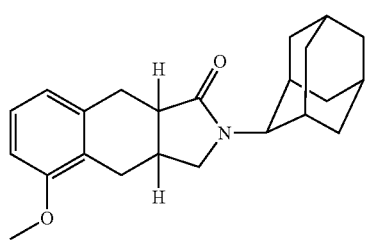
Co. No. 9; Ex. B2.
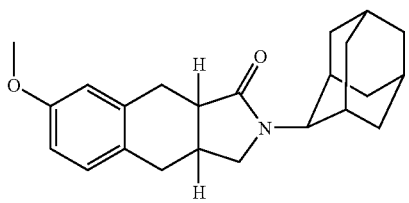
Co. No. 10; Ex. B2.
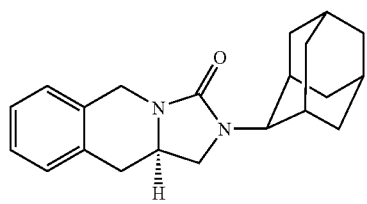
Co. No. 5; Ex. B5.
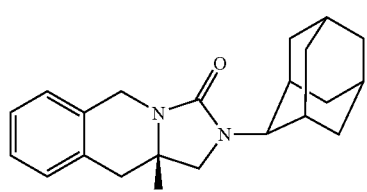
Co. No. 11; Ex. B5.
TABLE F-1-continued
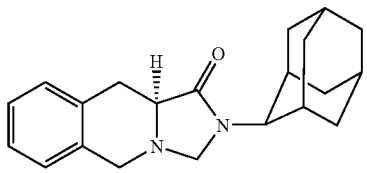
Co. No. 12; Ex. B4.
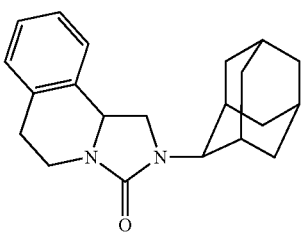
Co. No. 6; Ex. B6.
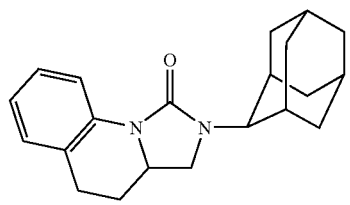
Co. No. 13; Ex. B6.
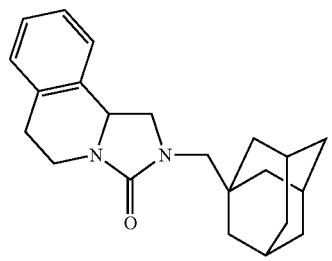
Co. No. 14; Ex. B6.
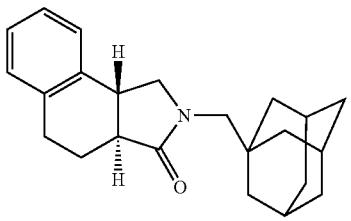
Co. No. 15; Ex. B3.
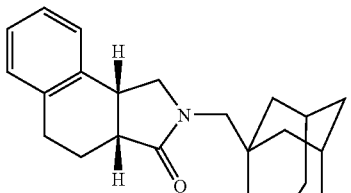
Co. No. 16; Ex. B3.

TABLE F-1-continued
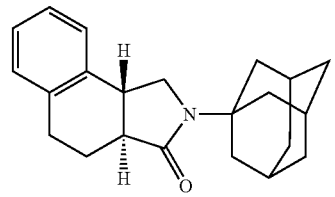
Co. No. 17; Ex. B3.
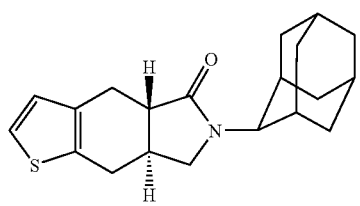
Co. No. 18; Ex. B2.
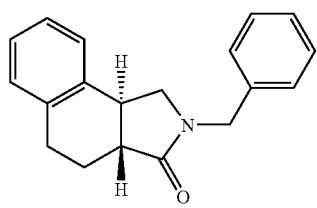
Co. No. 19; Ex. B3.
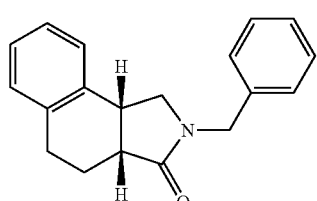
Co. No. 20; Ex. B3.
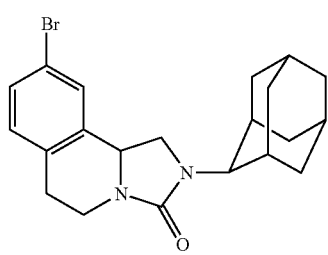
Co. No. 7; Ex. B7.
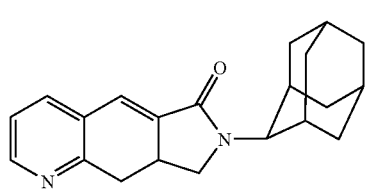
Co. No. 21; Ex. B2.
TABLE F-1-continued
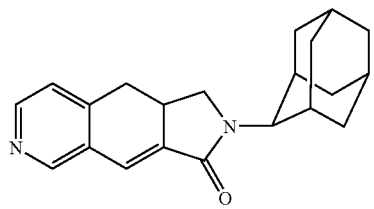
Co. No. 22; Ex. B2.
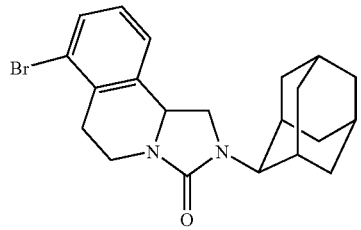
Co. No. 23; Ex. B7.
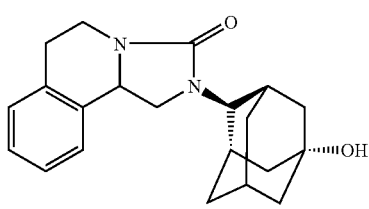
Co. No. 24; Ex. B6.
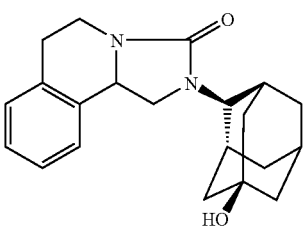
Co. No. 25; Ex. B6.
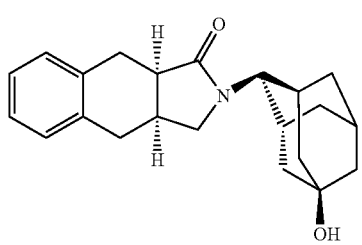
Co. No. 26; Ex. B2.
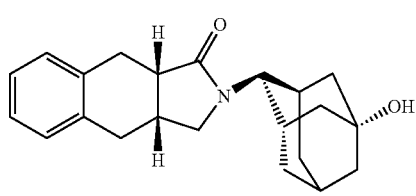
Co. No. 27; Ex. B2.

TABLE F-1-continued

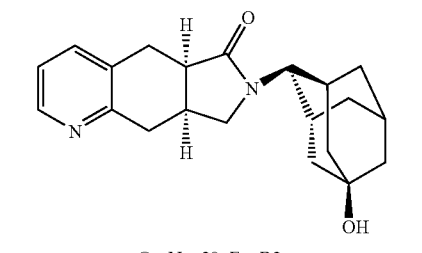

Co. No. 28; Ex. B2.

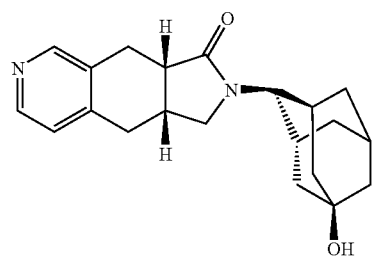

Co. No. 29; Ex. B2.

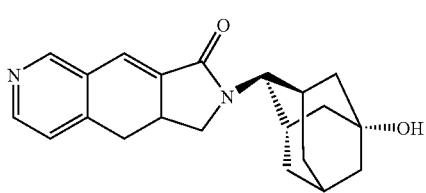

Co. No. 30; Ex. B2.

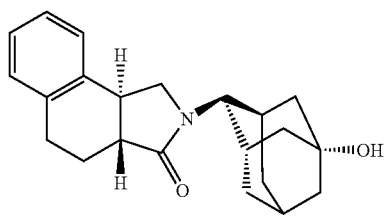

Co. No. 31; Ex. B3.

TABLE F-1-continued

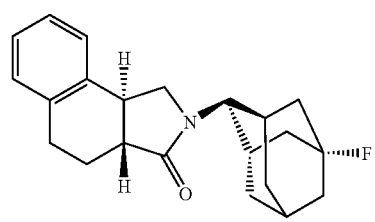

Co. No. 32; Ex. B3.

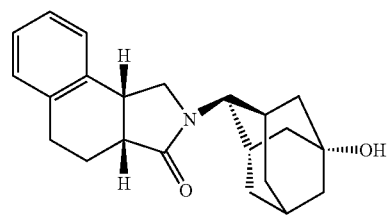

Co. No. 33; Ex. B3.

Co. No. 34; Ex. B2.

Table F-2 provides the $^1$H NMR and $^{13}$C NMR chemical shifts data for the compounds of the present invention using CDCl$_3$ as a solvent.

TABLE F-2

| Co. No. | NMR data | melting point (° C.) |
|---|---|---|
| 1 | 1H-NMR, CDCl$_3$; 1.48-1.98 (m, 16H, 14H-adamantane, 2H-CH2); 2.75 (m, 3H, CH$_2$, CH); 3.45 (dd, 1H, H$^A$-NCH$_2$); 3.62 (d, CH); 3.80 (dd, 1H, H$^B$-NCH$_2$); 3.96 (s, 1H-CH); 7.07 (d, 1H-aromatic); 7.15 and 7.25 (2xt, 2H-aromatic) 13C-NMR, CDCl3: 26.17; 27.82; 32.68; 33.00; 37.70; 37.99; 38.14; 51.12 (8xCH2); 27.12; 27.54; 30.96; 31.09; 31.56; 45.01; 58.83 (7xCH); 126.01; 126.34; 128.19; 130.68 (4xCH-aromatic); 131.89; 136.50 (C-ipso-aromatic); 174.39 C=O. | |
| 2 | 1H-NMR, CDCl$_3$; 1.53-1.95 (m, 14H-adamantane); 2.28 (dd, H$^A$-CH$_2$); 2.45 (m, 1H, CH); 2.55 (dd, H$^B$-CH$_2$); 2.65-2.79 (m, CH—C=O, H$^A$-CH$_2$); 2.93 (dd, H$^A$-NCH$_2$); 3.00 (m, H$^B$-CH$_2$); 3.40 (dd, H$^B$-NCH$_2$); 3.77 (s, 1H, CH); 6.95-7.15 (m, 4H-aromatic) | |
| 3 | 1H-NMR, CDCl$_3$; 1.61-2.12 (m, 14H-adamantane, H$^A$-CH$_2$); 2.20-2.43 (m, CH—C=O and H$^B$-CH$_2$); 2.80-3.12 (m, CH, CH$_2$); 3.55 (dd, H$^A$-NCH$_2$); 4.07 (s, CH); 4.18 (dd, H$^B$-NCH$_2$); 7.02-7.22 (m, 4H-aromatic) 13C-NMR, CDCl3: 22.22; 28.78; 32.76; 32.91; 37.68; 37.91; 38.20; 49.24 (8xCH2); 27.21; 27.54; 31.05; 31.27; 42.30; 45.42; 58.45 (7xCH); 124.04; 125.58; 126.78; 129.16 (4xCH-aromatic); 136.98; 137.26 (C-ipso-aromatic); 176.01 C=O. | |

TABLE F-2-continued

| Co. No. | NMR data | melting point (° C.) |
|---|---|---|
| 8 | 1H-NMR, CDCl$_3$; 1.55-2.25 (m, 14H-adamantane, CH$_2$); 2.70-(t, 2H, CH$_2$); 2.77 (m, 1H, CH—C═O); 3.51 (dd, H$^A$-NCH$_2$); 3.57 (m, CH); 4.01 (s, CH); 4.12 (dd, H$^B$-NCH$_2$); 7.08-7.18 (m, 4H-aromatic) | |
| 4 | 1H-NMR, CDCl$_3$; 1.59-2.30 (m, 14H-adamantane); 2.95-3.12 (m, 2H, CH$_2$); 3.30 (m, 1H, CH—C═O); 3.69 (d, H$^A$-NCH$_2$); 3.96 (d, H$^B$-CH$_2$); 3.99 (s, CH); 4.28 (dd, H$^A$-CH$_2$); 4.63 (d, H$^B$-CH$_2$); 7.08-7.22 (m, 4H-aromatic) | |
| 9 | mixture | |
| 10 | 1H-NMR, CDCl$_3$; 1.65-2.32 (m, 14H-adamantane, 2x CH); 2.68-2.73 (m, 2H, 2x H$^A$-CH$_2$); 2.95 (dd, H$^B$-CH$_2$); 3.17 (dd, H$^B$-CH$_2$); 3.35 (dd, H$^A$-NCH$_2$); 3.78 (s, 3H, CH$_3$); 3.80-3.92 (m, H$^B$-NCH$_2$); 4.06 (s, 1H, CH); 6.72 and 7.05 (2x m, 3H-aromatic) | |
| 5 | 1H-NMR, CDCl$_3$; 1.58-2.04 (m, 12H-adamantane); 2.35 and 2.46 (2x brs, 2x 1H-adamantane); 2.76-2.93 (m, 2H, CH$_2$); 3.31 (dd, 1H, H$^A$-CH$_2$); 3.66 (s, 1H, CH); 3.67-3.75 (m, 2H, CH, H$^B$-CH$_2$); 4.22 and 4.86 (2x d, H$^A$ and H$^B$-CH$_2$); 7.09-7.23 (m, 4H-aromatic) | |
| 11 | 1H-NMR, CDCl$_3$; 1.58-2.05 (m, 12H-adamantane); 2.45 and 2.55 (2x brs, 2x 1H-adamantane); 2.76-2.93 (m, 2H, CH$_2$); 3.33 (dd, 1H, H$^A$-CH$_2$); 3.66 (s, 1H, CH); 3.67-3.75 (m, 2H, CH, H$^B$-CH$_2$); 4.22 and 4.86 (2x d, H$^A$ and H$^B$-CH$_2$); 7.09-7.23 (m, 4H-aromatic) | |
| 12 | 1H-NMR, CDCl$_3$; 1.61-2.25 (m, 14H-adamantane); 2.96-3.11 (2xdd, 2H, CH$_2$); 3.30 (m, 1H, CH—C═O); 3.79 (d, H$^A$-CH$_2$); 3.96 (d, H$^B$-CH$_2$); 3.99 (s, CH); 4.28 (dd, H$^A$-CH$_2$); 4.64 (d, H$^B$-CH$_2$); 7.08-7.22 (m, 4H-aromatic) | |
| 6 | 1H-NMR, CDCl$_3$; 158-1.95 (m, 12H-adamantane); 2.22 and 2.50 (2x brs, 2x 1H-adamantane); 2.64 (m, 1H, H$^A$-CH$_2$); 2.96-3.11 (m, 2H, H$^B$-CH$_2$ and H$^A$-CH$_2$); 3.42 (dd, 1H, H$^A$-CH$_2$); 3.62 (s, 1H, CH); 4.04 (dd, 1H, H$^B$-CH$_2$); 4.12 (m, 1H, H$^B$-CH$_2$); 4.65 (t, 1H, CH); 7.07-7.25 (m, 4H-aromatic) | |
| 13 | 1H-NMR, CDCl$_3$; 1.61-2.12 (m, 14H, 12H-adamantane, CH$_2$); 2.15 and 2.53 (2x brs, 2x 1H-adamantane); 2.85 (dd, 1H, H$^A$-CH$_2$); 2.95 (m, 1H, H$^B$-CH$_2$); 3.24 (dd, H$^A$-NCH$_2$); 3.73 (s, 1H, CH); 3.81 (dd, H$^B$-NCH$_2$); 3.91 (m, 1H, CH); 6.91 and 7.17 (2xt, 2H-aromatic); 7.08 and 8.28 (2xd, 2H-aromatic) | |
| 14 | 1H-NMR, CDCl$_3$; 1.48-1.94 (m, 15H-adamantane); 2.65 (m, 2H, 2x H$^A$-CH$_2$); 2.96 (d, 1H, H$^B$-CH$_2$); 2.98-3.14 (m, 2H, H$^B$-CH$_2$ and H$^A$-CH$_2$); 3.35 (dd, 1H, H$^A$-CH$_2$); 3.98 (dd, 1H, H$^B$-CH$_2$); 4.12 (m, H$^B$-CH$_2$); 4.78 (t, 1h, CH); 7.08-7.24 (m, 4H-aromatic | |
| 15 | 1H-NMR, CDCl$_3$; 1.50-1.74 (m, 12H-adamantane); 1.80 (m, H$^A$-CH$_2$); 1.98 (brs, 3H, H-adamantane); 2.28 (dd, 1H, CH—C═O); 2.82-2.92 (m, 2H, CH$_2$); 2.89 and 3.16 (2xd, H$^A$ and H$^B$-CH$_2$); 2.93-3.12 (m, 3H, CH and CH$_2$); 3.58 (dd, H$^A$-NCH$_2$); 3.83 (dd, H$^B$-CH$_2$); 6.96 (d, 1H-aromatic); 7.12-7.21 (m, 3H-aromatic) | |
| 16 | 1H-NMR, CDCl$_3$; 1.40-1.94 (m, 15H-adamantane); 2.01 (m, CH$_2$); 2.65-2.76 (m, 3H, CH$_2$, H$^A$-CH$_2$); 2.82 (m, 1H, CH—C═O); 3.05 (d, H$^B$-CH$_2$); 3.39 (dd, H$^A$-CH$_2$); 3.58 (m, 1H, CH); 3.86 (dd, H$^B$-CH$_2$); 7.08-7.22 (m, 4H-aromatic) | |
| 17 | 1H-NMR, CDCl$_3$; 1.66-1.81 (m, 6H-adamantane, H$^A$-CH$_2$); 2.12-2.34 (m, 12H, 9H-adamantane, CH—C═O and H$^B$-CH$_2$); 2.88-3.08 (m, 3H, CH, CH$_2$); 3.32 (dd, H$^A$-NCH$_2$); 3.98 (dd, H$^B$-NCH$_2$); 6.98 (d, 1H-aromatic); 7.11-7.20 (m, 3H-aromatic) | |
| 18 | 1H-NMR, CDCl$_3$; 1.63-2.06 (m, 13H-adamantane); 2.20-2.43 (m, 3H, 1H-adamantane, CH$_2$); 2.58 and 2.74 (2x t, 2x CH); 3.07 (m, 2H, CH$_2$); 3.36 (dd, 1H, H$^A$-CH$_2$); 3.90 (dd, 1H, H$^B$-CH$_2$); 4.05 (s, CH), 6.84 and 7.13 (2x d, 2H-aromatic) | |
| 19 | 1H-NMR, CDCl$_3$; 1.78-1.92 (m, 1H, H$^A$-CH2); 2.32 (dt, 1H, H$^B$-CH2); 2.45 (m, 1H, CH—C═O); 2.94-3.16 (m, 3H, CH, CH$_2$); 3.39 (dd, 1H, H$^A$-NCH$_2$); 3.64 (dd, 1H, H$^B$-NCH$_2$); 4.55 (s, 2H, CH$_2$); 6.90 (d, 1H-aromatic); 7.07-7.36 (m, 8H-aromatic) | |
| 20 | 1H-NMR, CDCl$_3$; 1.92-2.09 (m, 2H, CH2); 2.72 (m, 2H, CH2); 2.89 (m, 1H, H$^A$-CH$_2$); 3.09 (dd, 1H, H$^A$-NCH$_2$); 3.60 (m, 1H, CH); 3.70 (dd, 1H, H$^B$-NCH$_2$); 4.47 (s, 2H, CH$_2$); 7.02-7.30 (m, 4H-aromatic) | |
| 7 | 1H-NMR, CDCl$_3$; 1.56-1.95 (m, 11H-adamantane); 2.24 and 2.46 (2x brs, 2x 1H-adamantane); 2.59 (m, 1H, H$^A$-CH$_2$); 2.85-3.06 (m, 2H, H$^B$-CH$_2$ and H$^A$-CH$_2$); 3.40 (dd, 1H, H$^A$-CH$_2$); 3.62 (s, 1H, CH); 4.04 (dd, 1H, H$^B$-CH$_2$); 4.12 (m, 1H, H$^B$-CH$_2$); 4.70 (t, 1H, CH); 7.00 and −7.22 (2x d, 2H-aromatic; 7.32 (dd, 1H-aromatic) | |
| 21 | 1H-NMR, CDCl$_3$; 1.69-2.07 (m, 12H-adamantane); 2.28 and 2.43 (2x brs, 2x 1H-adamantane); 2.84 (t, 1H, H$^A$-CH$_2$); 3.06-3.20 (m, 1H, CH); 3.25-3.39 (m, H$^B$-CH$_2$ and H$^A$-CH$_2$); 4.18 (s, 1H, CH); 4.21 (t, 1H, H$^B$-CH$_2$); 7.12 (d, 1H, ═CH); 7.19; 7.53 and 8.40 (3x dd, 3H-aromatic | |
| 22 | 1H-NMR, CDCl$_3$; 1.67-2.04 (m, 12H-adamantane); 2.26 and 2.43 (2x brs, 2x 1H-adamantane); 2.68 (t, 1H, H$^A$-CH$_2$); 2.92-3.10 (m, | |

TABLE F-2-continued

| Co. No. | NMR data | melting point (° C.) |
|---|---|---|
| | 2H, CH, $H^B$-CH$_2$); 3.32 (dd, 1H, $H^A$-CH$_2$); 4.18 (m, 2H, CH, $H^B$-CH$_2$); 7.16 (d, 1H, =CH); 7.21 and 8.43 (2x d, 2H-aromatic); 8.50 (s, 1H-aromatic) | |
| 23 | 1H-NMR, CDCl$_3$; 1.54-1.93 (m, 11H-adamantane); 2.23 and 2.47 (2x brs, 2x 1H-adamantane); 2.82 (m, 2H, CH$_2$); 2.98-3.07 (m, 1H, $H^A$-CH$_2$); 3.39 (dd, 1H, $H^A$-CH$_2$); 3.61 (s, 1H, CH); 4.03 (dd, 1H, $H^B$-CH$_2$); 4.18 (dt, 1H, $H^B$-CH$_2$); 4.72 (t, 1H, CH); 7.04 and −7.14 (m, 2H-aromatic; 7.49 (d, 1H-aromatic) | |
| 24 | 1H-NMR, CDCl$_3$; 1.40-2.35 (m, 13H, adamantane); 3.10 (m, 3H, CH$_2$, CH); 3.35 (t, 1H, $H^A$-NCH$_2$); 3.50 (s, CH); 4.00 (t, 1H, $H^B$-NCH$_2$); 4.10 (dd, 1H-CH); 4.75 (t, 1H, CH); 7.07 (d, 1H-aromatic); 7.15 and 7.25 (2xt, 2H-aromatic) | 235-237 |
| 25 | 1H-NMR, CDCl$_3$; 1.52-2.30 (m, 13H, adamantane); 3.05 (m, 3H, CH$_2$, CH); 3.45 (t, 1H, $H^A$-NCH$_2$); 3.45 (s, CH); 4.05 (t, 1H, $H^B$-NCH$_2$); 4.10 (dd, 1H, $H^B$-NCH$_2$); 4.75 (t, 1H-CH); 7.09 (d, 1H-aromatic); 7.13 and 7.22 (2xt, 2H-aromatic) | 210-212 |
| 26 | 1H-NMR, CDCl$_3$; 1.18-1.61 (m, 10H-adamantane); 2.08 and 2.32 and 2.43 (2x brs, 3H-adamantane); 2.58 (dd, 1H, $H^A$-CH$_2$); 2.69-3.15 (m, 5H, 2x CH, $H^B$-CH$_2$); 3.12 (dd, $H^A$-NCH$_2$); 3.59 (s, 1H, CH); 3.72 (dd, 1H, $H^B$-NCH$_2$); 7.14-7.21 (m, 4H-aromatic) | |
| 27 | 1H-NMR, CDCl$_3$; 1.45-1.84 (m, 10H-adamantane); 2.01 and 2.26 (brs, 3H-adamnatane); 2.56 (dd, 1H, $H^A$-CH$_2$); 2.70-3.03 (m, 5H, 2x CH, $H^B$-CH$_2$); 3.12 (dd, $H^A$-NCH$_2$); 3.68-3.76 (m, 2H, CH, $H^B$-NCH$_2$); 7.12-7.19 (m, 4H-aromatic) | |
| 28 | 1H-NMR, CDCl$_3$; 1.25, 1.37 (2x d, 2H-adamantane); 1.52-1.98 (m, 8H-adamantane); 2.08, 2.26, 2.35 (3x brs, 3H-adamantane); 2.80-3.15 (m, 6H, 2x CH, 2x CH2); 3.21 (dd, 1H, $H^A$-NCH$_2$); 3.63 (s, CH); 3.78 (dd, $H^B$-NCH$_2$); 7.12 (dd, 1H-aromatic), 7.45 and 8.46 (2x d, 2H-aromatic) | |
| 29 | 1H-NMR, CDCl$_3$; 1.34, 1.44 (2x d, 2H-adamantane); 1.52-1.94 (m, 8H-adamantane); 2.10 and 2.35 (2x brs, 3H-adamantane); 2.59 (dd, 1H, $H^A$-CH$_2$); 2.78-2.93 (m, 3H, CH, $H^A$-CH$_2$, $H^B$-CH$_2$); 2.96-3.08 (m, 2H, CH and $H^B$-CH$_2$); 3.13 (dd, 1H, $H^A$-NCH$_2$); 3.66 (s, CH); 3.78 (dd, $H^B$-NCH$_2$); 7.12 (d, 1H-aromatic), 8.41 (m, 2H-aromatic) | |
| 30 | 1H-NMR, CDCl$_3$; 1.52-1.99 (m, 11H-adamantane); 2.23 and 2.47 (2x brs, 2H-adamantane); 2.66-2.75 (m, 1H, $H^A$-CH$_2$); 2.93-3.11 (m, 2H, CH, $H^B$-CH$_2$); 3.28 (dd, 1H, $H^A$-NCH$_2$); 4.07 (s, CH); 4.14 (dd, $H^B$-NCH$_2$); 7.17 (d, 1H, =CH), 7.22 and 8.44 (2x d, 2H-aromatic); 8.50 (s, 1H-aromatic) | |
| 31 | 1H-NMR, CDCl$_3$; 1.50-2.02 (m, 11H-adamantane); 2.19-2.41 (m, 3H, CH—C=O and CH$_2$); 2.54 (brd, 2H-adamantane); 2.92-3.13 (m, 3H, CH, CH$_2$); 3.53 (dd, $H^A$-NCH$_2$); 3.98 (s, CH); 4.14 (dd, $H^B$-NCH$_2$); 7.02 (d, 1H-aromatic); 7.12-7.22 (m, 3H-aromatic) | |
| 32 | 1H-NMR, CDCl$_3$; 1.53-2.02 (m, 9H-adamantane); 2.10 and 2.63 (2x brd, 4H-adamantine); 2.22-2.40 (m, 3H, CH—C=O and CH$_2$); 2.92-3.12 (m, 3H, CH, CH$_2$); 3.52 (dd, $H^A$-NCH$_2$); 3.98 (s, CH); 4.10 (dd, $H^B$-NCH$_2$); 7.02 (d, 1H-aromatic); 7.12-7.22 (m, 3H-aromatic) | |
| 33 | 1H-NMR, CDCl$_3$; 1.42-2.01 (m, 10H, 9H-adamantane, $H^A$-CH$_2$); 2.12 and 2.43 (2x brs, 3H-adamantine); 2.71 (t, 2H, CH$_2$); 2.80 (m, 1H, CH—C=O); 3.43-3.51 (m, 2H, and $H^B$-CH$_2$) 3.61 (dd, $H^A$-NCH$_2$); 3.92 (s, 1H, CH); 4.06 (dd, $H^B$-NCH$_2$); 7.11-7.22 (m, 4H-aromatic) | |
| 34 | 1H-NMR, CDCl$_3$; 1.20-2.29 (m, 13H-adamantane); 2.59 (dd, 1H, $H^A$-CH$_2$); 2.78-2.93 (m, 3H, CH, $H^A$-CH$_2$, $H^B$-CH$_2$); 2.96-3.08 (m, 2H, CH and $H^B$-CH$_2$); 3.13 (dd, 1H, $H^A$-NCH$_2$); 3.71 (s, CH); 3.77 (dd, $H^B$-NCH$_2$); 7.09 (d, 1H-aromatic), 8.39 (m, 2H-aromatic) | |

C. Pharmacological Examples

Example C1

Enzymatic Assays to Test the Effect of Compounds on 11b-hydroxysteroid Dehydroganase Type 1 and Type 2

The effects of compounds on 11b-HSD1 dependent conversion of cortisone into cortisol (reductase activity) was studied in a reaction mixture containing 30 mM Tris-HCl buffer pH 7.2, 180 μM NADPH, 1 mM EDTA, 2 μM cortisone, 1 μl drug and/or solvent and 11 μg recombinant protein in a final volume of 100 μl.

The effect on the 11b-HSD1-dehydrogenase activity (conversion of cortisol into cortisone) was measured in a reaction mixture containing 0.1M sodium phosphate buffer pH 9.0, 300 μM NADP, 25 μM cortisol, 1 μl drug and/or solvent and 3.5 μg recombinant protein in a final volume of 100 μl.

The effects on the 11b-HSD2 dependent dehydrogenase activity was studied in a reaction mixture containing 0.1M sodium phosphate buffer pH 7.5, 300 μM NAD, 100 nM cortisol (of which 2 nM is 3H-radio labelled), 1 μl drug and/or solvent and 2.5 μg recombinant protein in a final volume of 100 μl.

All incubations were performed for 45 min at 37 C in a water bath. The reaction was stopped by adding 100 μl acetonitrile containing 20 μg corticosterone as internal standard. After centrifugation, the product formation was analysed in the supernatant by HPLC on a Hypersyl BDS-C18 column using 0.05 mM ammonium acetate/methanol (50/50) as solvent. In all of the aforementioned assays, the drugs to be tested were taken from a stock solution and tested at a final concentration ranging from $-10^{-5}$M to $3.10^{-9}$M. From the thus obtained dose response curves, the pIC50 value was calculated and scored as follows; Score 1=pIC50 value <5, Score 2=pIC50 value in the range of 5 to 6, Score 3=pIC50 value >6. Some of the thus obtained results are summarized in the table below. (in this table NT stands for Not Tested).

Example C2

Cellular Assays to Test the Effect of Compounds on 11b-hydroxysteroid Dehydroganase Type 1 and Type 2

The effects on 11b-HSD1 activity was measured in differentiated 3T3-L1 cells and rat hepatocytes.

Mouse fibroblast 3T3-L1 cells (ATCC-CL-173) were seeded at a density of 16500 cells/ml in 12 well plates and grown for 7 days in DMEM medium (supplemented with 10% heat inactivated foetal calf serum, 2 mM glutamine and 25 mg gentamycin) at 37° C. in a humidified 5% $CO_2$ atmosphere. Medium was refreshed twice a week. Fibroblasts were differentiated into adipocytes at 37° C. in a 5% $CO_2$ humidified atmosphere in growth medium containing 2 µg/ml insulin, 55 µg/ml IBMX and 39.2 µg/ml dexamethasone.

Primary hepatocytes from male rats were seeded on normal Falcon 12 well plates at a density of 250000 cells/well and incubated for 16 hours at 37° C. in a 5% $CO_2$ humidified atmosphere in DMEM-HAM's F12 medium containing 5% Nu-serum, 100 U/ml penicillin, 100 µg/ml streptomycin, 0.25 µg/ml amphotericin B, 50 µg/ml gentamycin sulfate, 5 µg/ml insulin and 392 ng/ml dexamethasone. Following a 4 hour pre-incubation with test compound, 0.5 µCi $^3$H-cortisone or dehydrocorticosterone, was added to the 3T3-L1 cultures. One hour later, the medium was extracted on Extrelut$^3$-columns with 15 ml diethyl ether and the extract was analysed by HPLC as described above. The effects of JNJ-compounds on rat hepatocyte HSD1 activity was measured after an incubation period of 90 minutes with 0.5 µCi$^3$H-dehydrocorticosterone. Corticosterone formation was analysed by HPLC.

The effects on 11b-HSD2 activity was studied in HepG2 and LCC-PK1-cells HepG2-cells (ATCC HB-8065) were seeded in 12 well plates at a density of 100,000 cells/ml and grown at 37° C. in a humidified 5% $CO_2$ atmosphere in MEM-Rega-3 medium supplemented with 10% heat inactivated foetal calf serum, 2 mM L-glutamine and sodium bicarbonate). Medium was refreshed twice a week.

Pig kidney cells (LCC-PK1, ATCC CRL-1392) were seeded at a density of 150,000 cells/ml in 12 well plates and grown at 37° C. in a humidified 5% $CO_2$ atmosphere in Medium 199 supplemented with Earls modified salt solution, 100 U/ml penicillin, 100 µg/ml streptomycin and 10% foetal calf serum. Medium was refreshed twice a week. Twenty four hours prior to the onset of the experiment, medium was changed by medium containing 10% charcoal stripped foetal calf serum.

Following a 4 hour pre-incubation with test compound, 0.5 µCi $^3$H-cortisol or corticosterone, was added to the cultures. One hour later, the medium was extracted on Extrelut$^3$-columns with 15 ml diethyl ether and the extract was analysed by HPLC as described above.

As for the enzymatic assays, the compounds to be tested were taken from a stock solution and tested at a final concentration ranging from $-10^{-5}$M to $3.10^{-9}$M. From the thus obtained dose response curves, the pIC50 value was calculated and scored as follows; Score 1=pIC50 value <5, Score 2=pIC50 value in the range of 5 to 6, Score 3=pIC50 value >6. Some of the thus obtained results are summarized in the table below. (in this table NT stands for Not Tested).

| Compound Number | [C2] HSD1 cellular 3T3-L1 Score | [C1] hHSD1 reductase Score | [C2] HSD2 cellular HepG2 Score |
|---|---|---|---|
| 1 | 2 | 2 | NT |
| 2 | 3 | 3 | 2 |
| 3 | 3 | 3 | 3 |
| 8 | 3 | 2 | 2 |
| 4 | 3 | 1 | 1 |
| 9 | 3 | 2 | 2 |
| 10 | 3 | 3 | 1 |
| 5 | 3 | 2 | 2 |
| 11 | 3 | NT | NT |
| 12 | 2 | NT | NT |
| 6 | 3 | 3 | 3 |
| 13 | 1 | 1 | 1 |
| 14 | 3 | 3 | 2 |
| 15 | 3 | 3 | 2 |
| 16 | 3 | 3 | 2 |
| 17 | 3 | 3 | 3 |
| 18 | 3 | 3 | 2 |
| 19 | 3 | 1 | NT |
| 20 | 3 | 2 | NT |
| 7 | 3 | 3 | NT |
| 21 | 3 | 1 | NT |
| 22 | 3 | 2 | NT |
| 23 | 3 | 3 | 3 |
| 24 | 3 | 3 | 3 |
| 25 | 3 | 2 | NT |
| 26 | 2 | 2 | 1 |
| 27 | 3 | 3 | 2 |
| 28 | 1 | 1 | 1 |
| 29 | 1 | 1 | 1 |
| 30 | 2 | 1 | 1 |
| 31 | 3 | 3 | 3 |
| 32 | 3 | 3 | 3 |
| 33 | 3 | 3 | 3 |
| 34 | 2 | 2 | NT |

D. Composition Examples

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable addition salt thereof.

Example D1

Film-Coated Tablets

Preparation of Tablet Core

A mixture of A.I. (100 g), lactose (570 g) and starch (200 g) was mixed well and thereafter humidified with a solution of sodium dodecyl sulfate (5 g) and polyvinyl-pyrrolidone (10 g) in about 200 ml of water. The wet powder mixture was sieved, dried and sieved again. Then there was added microcrystalline cellulose (100 g) and hydrogenated vegetable oil (15 g). The whole was mixed well and compressed into tablets, giving 10.000 tablets, each comprising 10 mg of the active ingredient.

Coating

To a solution of methyl cellulose (10 g) in denaturated ethanol (75 ml) there was added a solution of ethyl cellulose (5 g) in $CH_2Cl_2$ (150 ml). Then there were added $CH_2Cl_2$ (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinyl-pyrrolidone (5 g) and concentrated color suspension (30 ml) and the whole was homogenated. The tablet cores were coated with the thus obtained mixture in a coating apparatus.

The invention claimed is:

1. A compound having the formula

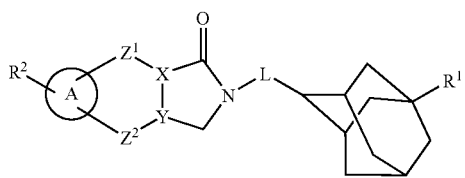

(I)

the N-oxide forms, the pharmaceutically acceptable addition salts and the stereochemically isomeric forms thereof, wherein X represents C;
Y represents C;
L represents a methyl or a direct bond;
$Z^1$ represents a direct bond and $Z^2$ represents $C_2$alkyl- or —$CH_2$—CH=, or
$Z^1$ represents a $C_1$alkyl- or —CH= and $Z^2$ represents $C_1$alkyl- or —CH=, or
$Z^1$ represents $C_2$alkyl- or —$CH_2$—CH= and $Z^2$ represents a direct bond;
$R^1$ represents hydrogen, halo, cyano, amino, phenyl, hydroxy, $C_{1-4}$alkyloxycarbonyl, —O—(C=O)—$C_{1-4}$alkyl, hydroxycarbonyl, $NR^3R^4$ or $C_{1-4}$alkyl wherein said $C_{1-4}$alkyl or —O—(C=O)—$C_{1-4}$alkyl are optionally substituted with one or more substituents selected from halo, hydroxycarbonyl, phenyl, $C_{1-4}$alkyloxy or $NR^5R^6$ or
$R^1$ represents $C_{1-4}$alkyloxy- optionally substituted with one or more substituents selected from halo, hydroxycarbonyl, phenyl, $C_{1-4}$alkyloxy or $NR^7R^8$;
$R^2$ represents hydrogen, halo, $C_{1-4}$alkyl or $C_{1-4}$alkyloxy-;
$R^3$ and $R^4$ each independently represent hydrogen, $C_{1-4}$alkyl or $C_{1-4}$alkylcarbonyl-;
$R^5$ and $R^6$ each independently represent hydrogen, $C_{1-4}$alkyl or $C_{1-4}$alkylcarbonyl-;
$R^7$ and $R^8$ each independently represent hydrogen, $C_{1-4}$alkyl or $C_{1-4}$alkylcarbonyl-; and
A represents phenyl.

2. A compound according to claim 1 wherein;
L represents a methyl or a direct bond;
$R^1$ represents hydrogen, halo, cyano, amino, phenyl, hydroxy, $C_{1-4}$alkyloxycarbonyl, hydroxycarbonyl, $NR^3R^4$ or $C_{1-4}$alkyl optionally substituted with one or more substituents selected from hydroxycarbonyl, phenyl, $C_{1-4}$alkyloxy or $NR^5R^6$ or $R^1$ represents $C_{1-4}$alkyloxy- optionally substituted with one or more substituents selected from hydroxycarbonyl, phenyl, $C_{1-4}$alkyloxy or $NR^7R^8$;
$R^2$ represents hydrogen, halo, $C_{1-4}$alkyl or $C_{1-4}$alkyloxy-;
$R^3$ and $R^4$ each independently represent hydrogen, $C_{1-4}$alkyl or $C_{1-4}$alkylcarbonyl-;
$R^5$ and $R^6$ each independently represent hydrogen, $C_{1-4}$alkyl or $C_{1-4}$alkylcarbonyl-; and
$R^7$ and $R^8$ each independently represent hydrogen, $C_{1-4}$alkyl or $C_{1-4}$alkylcarbonyl-.

3. A compound according to claim 1 wherein;
L represents methyl or a direct bond;
$R^1$ represents hydrogen, halo or hydroxy; and
$R^2$ represents hydrogen, halo or $C_{1-4}$alkyloxy-.

4. A compound according to claim 1 wherein L represents a direct bond; and
$R^1$ represents halo, cyano, amino, phenyl, hydroxy, $C_{1-4}$alkyloxycarbonyl-, hydroxycarbonyl, $NR^3R^4$ or $C_{1-4}$alkyl substituted with one or more substituents selected from hydroxycarbonyl, phenyl, $C_{1-4}$alkyloxy or $NR^5R^6$.

5. A compound selected from the group consisting of;
2-Adamantan-2-yl-2,3,3a,4,9,9a-hexahydro-benzo[f]isoindol-1-one;
2-Adamantan-2-yl-2,3,10,10a-tetrahydro-5H-imidazo[1,5-b]isoquinolin-1-one;
2-Adamantan-2-yl-1,5,10,10a-tetrahydro-2H-imidazo[1,5-b]isoquinolin-3-one;
2-Adamantan-1-ylmethyl-1,2,3a,4,5,9b-hexahydro-benzo[e]isoindol-3-one;
7-Adamantan-2-yl-7,8,8a,9-tetrahydro-pyrrolo[3,4-g]quinolin-6-one;
2-(5-Hydroxy-adamantan-2-yl)-1,5,6,10b-tetrahydro-2H-imidazo[5,1-a]isoquinolin-3-one;
2-(5-Fluoro-adamantan-2-yl)-1,2,3a,4,5,9b-hexahydro-benzo[e]isoindol-3-one; and
2-(5-Hydroxy-adamantan-2-yl)-2,3,3a,4,9,9a-hexahydro-benzo[f]isoindol-1-one; or
a pharmaceutically acceptable addition salt thereof.

6. A pharmaceutical composition comprising a pharmaceutically acceptable carrier and, as active ingredient, an effective 11β-HSD1 inhibitory amount of a compound as described in claim 1.

7. A process of preparing a pharmaceutical composition as defined in claim 6, said pharmaceutically acceptable carrier is intimately mixed with said effective 11β-HSD1 inhibitory amount of said compound.

8. A method for treating obesity or diabetes comprising administering an effective amount of a compound of claim 1 to a warm blooded animal suffering from obesity or diabetes.

9. A compound of formula

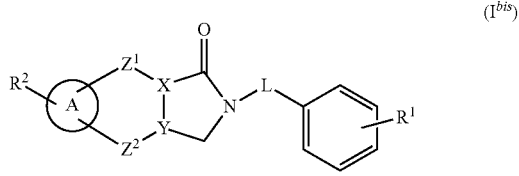

(I$^{bis}$)

the N-oxide forms, the pharmaceutically acceptable addition salts and the stereochemically isomeric forms thereof, wherein X represents C;
Y represents C;
L represents a methyl or a direct bond;
$Z^1$ represents a direct bond and $Z^2$ represents $C_2$alkyl- or —$CH_2$—CH=, or
$Z^1$ represents a $C_1$alkyl- or —CH= and $Z^2$ represents $C_1$alkyl- or —CH=, or $Z^1$ represents $C_2$alkyl- or —$CH_2$—CH= and $Z^2$ represents a direct bond;

$R^1$ represents hydrogen, halo, cyano, amino, phenyl, hydroxy, $C_{1-4}$alkyloxycarbonyl, —O—(C=O)—$C_{1-4}$alkyl, hydroxycarbonyl, $NR^3R^4$ or $C_{1-4}$alkyl wherein said $C_{1-4}$alkyl or —O—(C=O)—$C_{1-4}$alkyl are optionally substituted with one or more substituents selected from halo, hydroxycarbonyl, phenyl, $C_{1-4}$alkyloxy or $NR^5R^6$ or $R^1$ represents $C_{1-4}$alkyloxy- optionally substituted with one or more substituents selected from halo, hydroxycarbonyl, phenyl, $C_{1-4}$alkyloxy or $NR^7R^8$;

$R^2$ represents hydrogen, halo, $C_{1-4}$alkyl or $C_{1-4}$alkyloxy-;

$R^3$ and $R^4$ each independently represent hydrogen, $C_{1-4}$alkyl or $C_{1-4}$alkylcarbonyl-;

$R^5$ and $R^6$ each independently represent hydrogen, $C_{1-4}$alkyl or $C_{1-4}$alkylcarbonyl-;

$R^7$ and $R^8$ each independently represent hydrogen, $C_{1-4}$alkyl or $C_{1-4}$alkylcarbonyl-; and A represents phenyl.

10. A pharmaceutical composition comprising a pharmaceutically acceptable carrier and, as active ingredient, an effective 11β-HSD1 inhibitory amount of a compound as described in claim 9.

11. A method for treating obesity or diabetes comprising administering an effective amount of a compound of claim 9 to a warm blooded animal suffering from obesity or diabetes.

12. A method for treating insulin resistance, dyslipidemia, obesity or hypertension comprising administering an effective amount of a compound as claimed in claim 1 in combination with an antihypertensive agent to a warm blooded animal suffering from insulin resistance, dyslipidemia, obesity or hypertension.

13. A method for treating insulin resistance, dyslipidemia, obesity or hypertension comprising administering an effective amount of a compound as claimed in claim 9 in combination with an antihypertensive to a warm blooded animal suffering from insulin resistance, dyslipidemia, obesity or hypertension.

14. A compound having the following formula

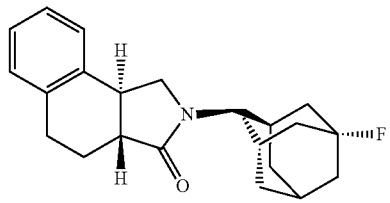 [SMILES: O=C1[C@@H]2CCc3ccccc3[C@H]2CN1[C@H]1[C@@H]2CC3C[C@H]1C[C@](F)(C3)C2]

or a pharmaceutically acceptable addition salt thereof.

* * * * *